United States Patent
Daniels et al.

(10) Patent No.: US 11,955,216 B2
(45) Date of Patent: Apr. 9, 2024

(54) MEDICATION STORAGE AND CLOSURE CONTAINER, MEDICATION DELIVERY STATION FOR DELIVERY OF MEDICATION FROM A REPLACEABLE PRE-FILLED MEDICATION STORAGE AND CLOSURE CONTAINER, AUTOMATED AND ADAPTABLE REMOTE MEDICATION MANAGEMENT SYSTEM INCLUDING A MEDICATION DELIVERY STATION, AND METHODS OF OPERATING AND/OR UTILIZING THE SAME

(71) Applicant: Zig Therapeutics, Inc., Carmel, IN (US)

(72) Inventors: Vicki L. Daniels, Carmel, IN (US); Joseph C. Steven, New Berlin, WI (US)

(73) Assignee: Zig Therapeutics, Inc., Carmel, IN (US)

( * ) Notice: Subject to any disclaimer, the term of this patent is extended or adjusted under 35 U.S.C. 154(b) by 0 days.

(21) Appl. No.: 18/130,715

(22) Filed: Apr. 4, 2023

(65) Prior Publication Data

US 2023/0317232 A1    Oct. 5, 2023

Related U.S. Application Data

(60) Provisional application No. 63/326,990, filed on Apr. 4, 2022.

(51) Int. Cl.
| | | |
|---|---|---|
| *G16H 20/13* | (2018.01) | |
| *G16H 40/20* | (2018.01) | |
| *G16H 40/63* | (2018.01) | |

(52) U.S. Cl.
CPC ............ *G16H 20/13* (2018.01); *G16H 40/20* (2018.01); *G16H 40/63* (2018.01)

(58) Field of Classification Search
CPC ......... G16H 20/13; G16H 40/20; G16H 40/63
See application file for complete search history.

(56) References Cited

U.S. PATENT DOCUMENTS

| | | |
|---|---|---|
| 2,199,242 A | 4/1940 | Ladd |
| 4,127,190 A | 11/1978 | Abbotoy |
| (Continued) | | |

FOREIGN PATENT DOCUMENTS

WO       2016127051 A1     8/2016

OTHER PUBLICATIONS

International Search Report and Written Opinion of the International Search Authority dated Jul. 31, 2023, received in connection with International Application No. PCT/US2023/017437 filed Apr. 4, 2023.

(Continued)

*Primary Examiner* — Michael Collins
(74) *Attorney, Agent, or Firm* — Boardman & Clark LLP

(57) ABSTRACT

A portable remote medication management system for automated and adaptive precision dosing is disclosed. The system includes a medication delivery station comprising a receptacle that stores a pre-filled replaceable medication storage and closure container. The pre-filled medication container can store oral solid medication in storage silos above a rotary release mechanism and contains a storage and communication chip that communicates with the delivery station. The medication delivery station includes a delivery housing, a drive and control mechanism, communication interfaces with the container closure and remote devices, and a removable medication receptacle within the delivery station. The medication delivery station and medication closure container connect mechanically through a drive interface under the control of the station. Dosing parameter adjustments can be controlled by an administration portal and (Continued)

uploaded to the medication delivery station, as commanded by the administrator. Also disclosed are method operating the system and devices.

24 Claims, 22 Drawing Sheets

(56) References Cited

U.S. PATENT DOCUMENTS

| | | | |
|---|---|---|---|
| 4,924,612 A * | 5/1990 | Kopelman | G09F 9/305 362/559 |
| 5,522,525 A | 6/1996 | McLaughlin | |
| 5,810,198 A | 9/1998 | Townsend et al. | |
| 7,108,153 B2 | 9/2006 | Wood | |
| 7,341,145 B2 | 3/2008 | Vandenbroek et al. | |
| 7,630,790 B2 * | 12/2009 | Handfield | A61J 7/0084 700/241 |
| 7,885,725 B2 | 2/2011 | Dunn | |
| 8,060,246 B2 | 11/2011 | Berg | |
| 8,108,068 B1 * | 1/2012 | Boucher | G01G 17/00 700/240 |
| 8,483,872 B2 | 7/2013 | Ratnakar | |
| 8,548,623 B2 | 10/2013 | Poutiatine et al. | |
| 9,501,626 B2 * | 11/2016 | Zhang | G16H 20/13 |
| 9,572,748 B2 | 2/2017 | Lim | |
| 9,836,583 B2 * | 12/2017 | García | G07F 11/54 |
| 9,901,515 B2 | 2/2018 | Roberts | |
| 10,104,904 B2 * | 10/2018 | Holman | A23P 10/00 |
| 10,426,707 B2 | 10/2019 | Hsu | |
| 10,588,824 B2 | 3/2020 | Hsu | |
| 10,709,643 B2 | 7/2020 | Hsu | |
| 10,849,829 B2 | 12/2020 | Bukstein | |
| 11,357,704 B2 * | 6/2022 | Duda | A61J 7/0418 |
| 11,410,764 B1 * | 8/2022 | Rosomoff | A61J 7/0076 |
| 11,510,849 B2 | 11/2022 | Bukstein et al. | |
| 2003/0183642 A1 * | 10/2003 | Kempker, Sr. | G07F 13/06 221/2 |
| 2005/0172964 A1 | 8/2005 | Anderson et al. | |
| 2007/0156282 A1 | 7/2007 | Dunn | |
| 2007/0186923 A1 | 8/2007 | Poutiatine | |
| 2008/0035520 A1 * | 2/2008 | Caracciolo | G07F 17/0092 206/535 |
| 2008/0203107 A1 | 8/2008 | Conley et al. | |
| 2009/0020549 A1 | 1/2009 | Lyndegaard et al. | |
| 2009/0127157 A1 | 5/2009 | Costa et al. | |
| 2009/0218363 A1 * | 9/2009 | Terzini | B65B 5/103 221/4 |
| 2010/0253476 A1 | 10/2010 | Poutiatine | |
| 2011/0170655 A1 | 7/2011 | Yuyama et al. | |
| 2012/0003928 A1 | 1/2012 | Geboers et al. | |
| 2012/0259457 A1 * | 10/2012 | Handfield | A61J 7/0084 700/237 |
| 2013/0116818 A1 | 5/2013 | Hamilton | |
| 2014/0244033 A1 | 8/2014 | Ucer et al. | |
| 2014/0277702 A1 | 9/2014 | Shaw | |
| 2015/0266654 A1 | 9/2015 | Baarman et al. | |
| 2015/0278479 A1 | 10/2015 | Ervin | |
| 2015/0291344 A1 | 10/2015 | MacVittie et al. | |
| 2016/0228333 A1 | 8/2016 | Bukstein et al. | |
| 2017/0074717 A1 | 3/2017 | Pilkington et al. | |
| 2017/0199983 A1 * | 7/2017 | Cano | A61J 7/02 |
| 2018/0060525 A1 * | 3/2018 | Chen | B65B 37/18 |
| 2019/0142698 A1 | 5/2019 | Bukstein et al. | |
| 2020/0103270 A1 | 4/2020 | Pilkington et al. | |
| 2021/0038477 A1 | 2/2021 | Bukstein et al. | |

OTHER PUBLICATIONS

FDA's Remote Medication Management https://www.fda.gov/medical-devices/guidance-documents-medical-devices-and-radiation-emitting-products/remote-medication-management-system-class-ii-special-controls-guidance-industry-and-fda-staff as of Nov. 15, 2023.
FDA's Combination Product Definition https://www.fda.gov/combination-products/about-combination-products/combination-product-definition-combination-product-types as of Nov. 15, 2023.
IPill Dispenser—https://www.ipilldispenser.com as of Nov. 15, 2023.
InRange Medication Management (Emma Health Technologies): https://www.emmahealthtech.com, as of Nov. 15, 2023.
Hero Health—https://herohealth.com/our-product/ as of Nov. 15, 2023.
Med Minder—https://www.medminder.com/ as of Nov. 15, 2023.
Livi—https://www.liviathome.com as of Nov. 15, 2023.
Emme https://emme.com as of Nov. 15, 2023.

* cited by examiner

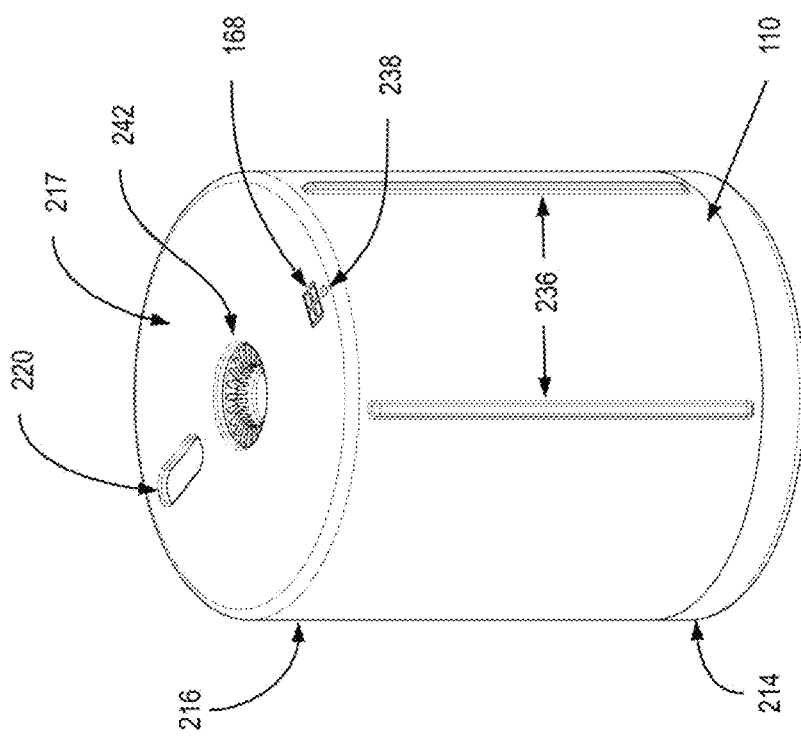
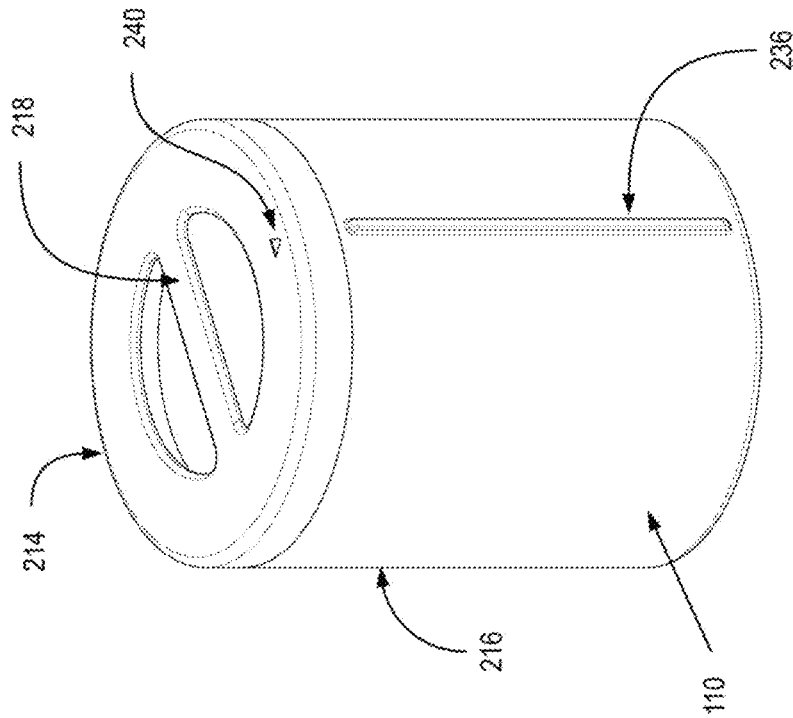

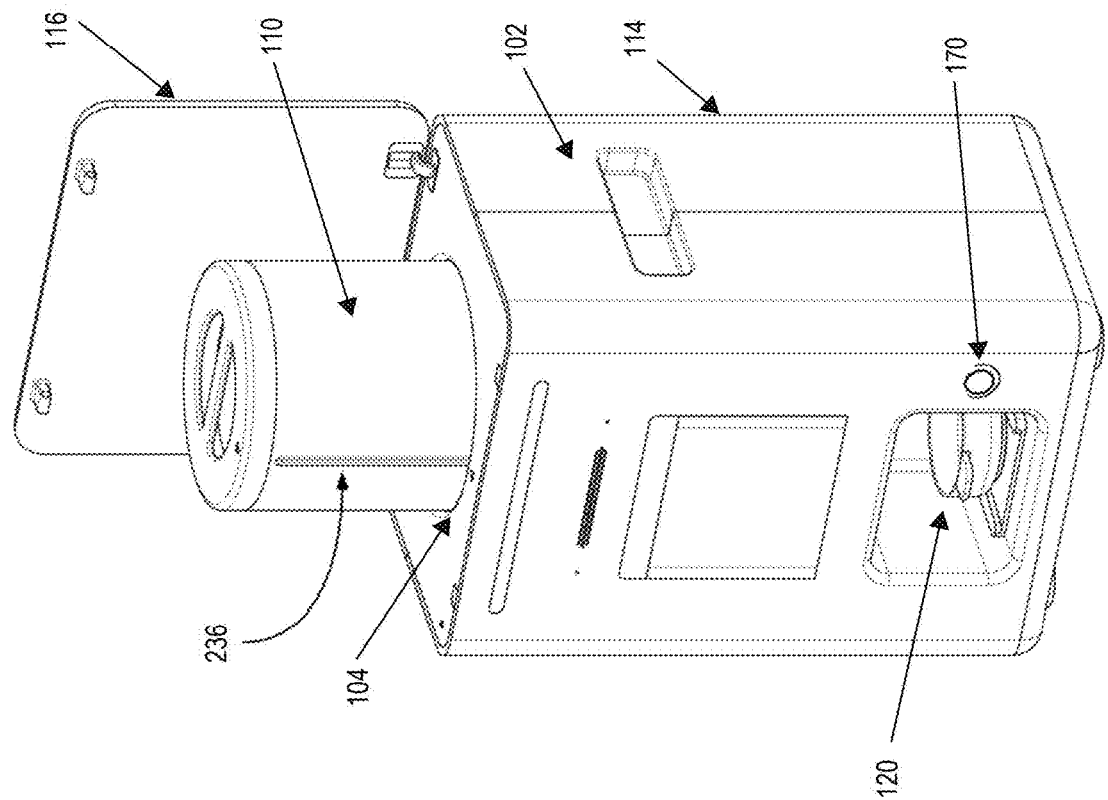
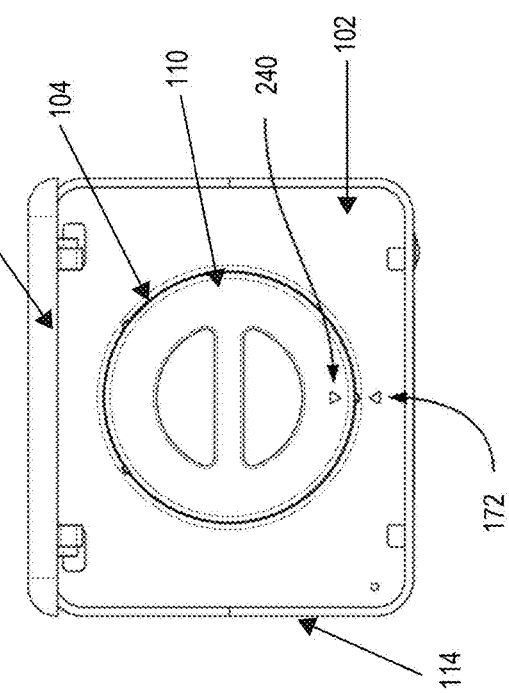
FIG. 9A
FIG. 9B

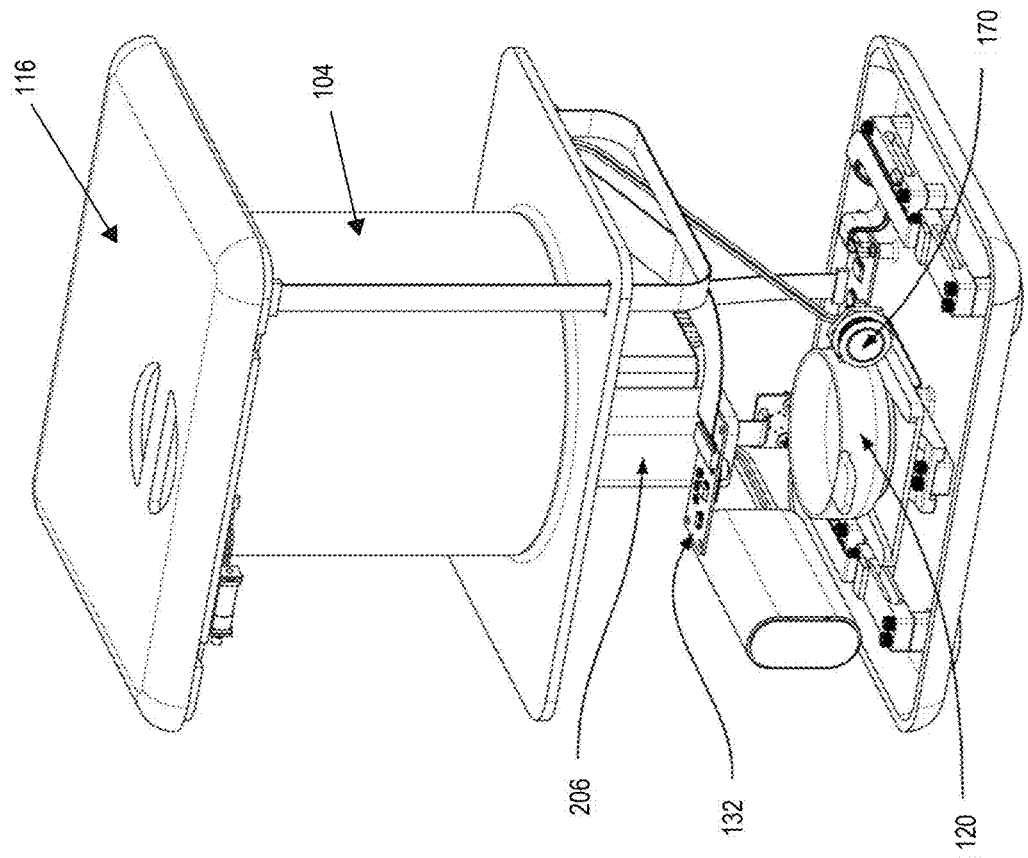
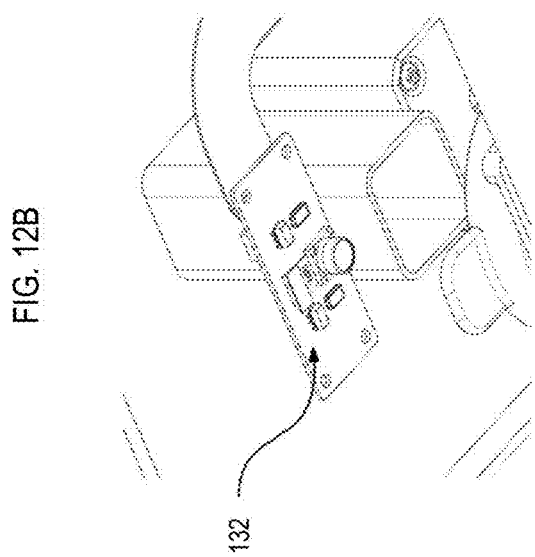
FIG. 12A
FIG. 12B

MEDICATION STORAGE AND CLOSURE CONTAINER, MEDICATION DELIVERY STATION FOR DELIVERY OF MEDICATION FROM A REPLACEABLE PRE-FILLED MEDICATION STORAGE AND CLOSURE CONTAINER, AUTOMATED AND ADAPTABLE REMOTE MEDICATION MANAGEMENT SYSTEM INCLUDING A MEDICATION DELIVERY STATION, AND METHODS OF OPERATING AND/OR UTILIZING THE SAME

RELATED APPLICATION

This application claims the benefit of U.S. Patent Application No. 63/326,990, entitled "REMOTE MEDICATION MANAGEMENT FOR ADAPTABLE PRECISION DOSING," filed Apr. 4, 2022, the entire content of which is incorporated herein by reference.

FIELD

This disclosure relates to remote medication management systems. The disclosure more specifically relates to automated and adaptable remote medication management systems for a patient.

BACKGROUND

The goal of selecting the right medication and dosing regimen for a patient is an ever-present challenge for clinicians. Clinicians often prescribe a medication dosing regimen based on, among other things, regulatory-approved dose labeling, professional society guidelines, and institutional decision support tools. A response by an individual to a specific medication can be vastly different from others due to patient-specific factors such as genetics, body mass index, drug interactions, diet, environment, co-morbidities, and metabolic processes, and drug-specific factors such as narrow therapeutic index and high inter-patient pharmacokinetic variability. Drug therapeutic responses can also differ due to a lack of adherence by the individual to the dosing regimen including missed doses, over-and-under dosing, and taking the dose at the wrong time. Some medications require response-based titration to determine the minimum optimal dose for an individual patient to achieve the targeted therapeutic effect. When patients take multiple medications, drug-to-drug interactions becomes a factor in prescribing one or more drug dosing regimens. Every year, individuals experience challenges related to a nonoptimal dosing regimen for an individual patient.

Recognizing the limitations of "one-size-fits-all" approach to dosing, clinicians often undertake a time-consuming and resource-intensive approach to select the dosing regimen for an individual patient to achieve maximal efficacy and minimal toxicity. Initially, clinicians often prescribe a dose based on patient-specific characteristics, clinician preferences, and formulary constraints with a follow-up office visit to access the initial treatment response. Subsequent medication treatment and dose modifications are made based on clinician judgement. In some cases, laboratory tests are needed to determine blood and serum levels for an appropriate therapeutic response. In other situations, the clinician relies on the accurate perceptual assessment of the patient and longitudinal memory recall of disease symptoms and quality of life measures to evaluate the need for dosing adjustments. Patient-reported medication side effects can also be reported to the clinician to inform the need for a dosing adjustment. Patient and caregiver medication errors can also impact drug exposure and response such as taking the wrong dose at the wrong time. When patients do not adhere to the prescribed dosing regimen, laboratory tests and patient-reported assessments do not provide the clinician with accurate information about the therapeutic response of a particular dosing regimen. For patients, medication adjustments can require additional office visits and lab tests, time away from work and school, result in avoidable care visits, and lead to nonoptimal quality of life. This trial-and-error dosing adjustment approach can be inaccurate, costly, and time-consuming for both patients and clinicians. The approach often results in protracted time to adequate treatment outcomes, simultaneous use of multiple medications, and patient nonadherence to treatment regimens.

Precision dosing (also referred to as individualized dosing) is the process of individualizing medication dosing regimens by considering patient-specific factors, drug attributes, genetic data, and disease state characteristics to optimize drug therapy. To date, real-time precision dosing at the individual patient level has been not practical or implementable for several reasons. However, healthcare payers and government agencies are recognizing the importance of remote therapeutic drug monitoring of a response of the patient to a medication dosing regimen. The Centers for Medicare and Medicaid Services (CMS) recently announced a new program to reimburse clinicians for the remote therapeutic monitoring of a response of the patient to a drug. The U.S. Federal Drug Administration (FDA) hosted a workshop on precision dosing to define the need and approaches for delivering individual drug dosing in real-world settings. In 2014, the Office of Disease Prevention and Health Promotion (ODPHP), of the U.S. Human and Human Services Agency released the National Action Plan for Adverse Drug Event Prevention to engage in strategies that help in the prevention of adverse drug events including use of clinical decision support, real-time data reporting of adverse drug events, and data repositories.

SUMMARY

Because of the above issues and others, there is a need for an improved automated and adaptable remote medication management system for precision dosing system to aid clinicians in determining individualized drug dosing regimens. In at least one implementation, the system can connect patients from their home or remote care facility to the healthcare providers and also ensure patients strict adherence to a dynamic medication dosing regimen that changes over time based on their individual therapeutic response to a medication. Accordingly, a remote medication management system for automated and adaptable precision dosing is provided, as well as a method for using the same.

In one or more implementations, an automated remote medication management system for precision dosing is disclosed. The remote medication management system attempts to be tamper-proof and uses a medication delivery station with electrical and electronic controls, communication hardware, monitoring software, and one or more pre-filled medication storage and closure containers to deliver the pre-specified, patient-specific dosing regimen in the exact prescribed quantities during specific prescribed time windows. A mobile application communicates with the medication delivery station and prompts the patient to release the scheduled dose using the station release (or actuation) button. The remote medication management system remains under the control and monitoring of a remote administrator. Remote monitoring of the adaptable medication management system including actuation, dosage, and frequency and timing of dosing is monitored and controlled by an administration portal. In addition to monitoring of one or more, or all the above features, two-way communication between the station and the remote administrator via a cellular or other wireless signal may also be provided to allow the remote administrator the ability to adjust any of the dosing regimen parameters remotely and receive real-time feedback on its use.

In further or alternative implementations, a remote medication management system for automated and adaptive precision dosing is disclosed. The system includes a plug-in medication delivery station comprising a medication delivery station with one or more pre-filled, tamper-proof, replaceable medication storage and closure container. The pre-filled medication container stores oral solid medication with a storage and communication chip that contains a medication-specific identifier including National Drug Code (NDC), a container-specific serial code or identifier, and pre-filled pill inventory count stored inside the container at activation. The medication delivery station includes a delivery drive and control mechanism, delivery housing, pill releasing sub-system, and communication interfaces. A third-party communication host is in communication with the delivery station. The delivery station has administration software or firmware with executable instructions for control of the delivery drive and control mechanism to release the prescribed medications to a removable medication cup. The medication delivery station communication interface is in communication with the third-party communication host and the patient mobile application on a mobile device such as a smart phone. Dosing parameter adjustments are controlled by the remote administration software and uploaded to the medication delivery station via the third-party host, as commanded by the remote administrator.

A replaceable medication closure container is also disclosed. The replaceable medication closure container stores medication in spring-loaded silos above a rotary release mechanism and interfaces with the medication delivery station to release the prescribed dosing as controlled by the delivery station administration software.

In one or more implementations, the medication closure container has a drive system interface, release aperture, rotary plate position locating features and a storage and communication chip that interface with the medication delivery station. The delivery station receptacle can include alignment rails on the replacement medication container to provide visual and palpable feedback to the user for proper alignment prior to and during insertion of the container into the receptacle. The drive system interface contains self-centering features to correct any minor misalignment during the meshing of the station and container components.

The release aperture on the closure container can be positioned in alignment with the pill chute in the receptacle, and the position witness hole allows locating features on the rotating plate within the container closure to align with the corresponding optical sensor in the receptacle for positional feedback during operation.

The storage and communication chip can contain a medication-specific identifier, and a write-back inventory status and the current dosing regimen. The chip can be interrogated by the delivery station controller upon insertion and during each dosing operation to validate closure container contents and to write back updated inventory status after the release of a scheduled dose. Seal features and desiccant within the closure container help ensure proper humidity control within the container.

A mobile application is also disclosed. The mobile application communicates with the medication delivery station and, in some cases, the third-party host. Medication dosing regimens include dose strength, number of pills per dose, dosing scheduling, and medication duration. The application can also provide medication instructions for use, automated medication reminders, an electronic copy of the prescription label, and refill schedules which are displayed to the patient through mobile app screens and real-time notifications.

In some embodiments, the patient provides side effects and symptom data to the remote administrator. For better medication adherence, the mobile application, in some implementations, assists the patient in providing a camera-image of the administration of the medication into their mouth and the swallowing of the medication using the mobile device embedded camera and illumination system. In some embodiments, remote physiological monitoring devices such as wearables, mobile medical devices, and patches can connect with the mobile application. Physiological data can be streamed to mobile electronic device and the mobile application can transfer the data to the remote administration portal.

A method for control and monitoring the dosing of medication is also provided. The method includes, in one or more implementations, connecting the medication delivery station with a third-party host, and once paired, automatically communicating the prescribed medication dosing regimen for the patient to the delivery station. Following the patient inserting the medication closure container into the delivery station receptacle, the closure container storage and communication chip pairs with the medication delivery station, and automatically confirms the prescription unique identifier codes, medication identification, and medication inventory status are synchronized between the container and the station. Upon receipt of pairing, the administrator has the ability to adjust in real-time the dosing parameters (e.g., dose, number of doses per day, and the time for each dose), modify the dosing at the individual pill level, and receive real-time feedback on the medication adherence by the patient. The method includes querying whether a release button has been depressed and operating the delivery station to deliver a predetermined quantity of medication according to the dosing regimen.

In one embodiment, the disclosure provides a medication storage and closure container comprising a plurality of doses of a medication, a sealed housing having a first aperture in the housing allowing for discharge of the plurality of doses, a structure coupled within the housing and supporting the plurality of doses, a closure opening and sealing the housing at the first aperture, a communication interface coupled to the housing, and a read-write memory coupled to the communication interface. The memory includes information having a container-specific identifier, a medication-specific identifier, and a medication inventory status.

In another embodiment, the disclosure provides a medication delivery station for delivery of medication from a replaceable pre-filled medication storage and closure container having a first communication interface. The station comprising a housing having a receptacle to receive the replaceable pre-filled medication storage and closure container and a dispenser to dispense the medication, a second communication interface supported by the housing and to communicate with the first communication interface, and a processor and a memory in communication with the processor. The memory including instructions executable by the processor to communicate with the container via the second communication interface and the first communication interface, and receive information related to the container including a container-specific identifier, a medication-specific identifier, and a medication inventory status.

In yet another embodiment, the disclosure provides a medication management system comprising a replaceable pre-filled oral solid medication storage and closure container and a medication delivery station. The medication closure container can include a plurality of pills, a sealed housing having a first aperture in the housing allowing for discharge of the plurality of pills, a closure opening and sealing the sealed housing at the first aperture, a first communication interface coupled to the sealed housing, and a read-write memory coupled to the first communication interface. The read-write memory has information including a container-specific identifier, a medication-specific identifier, and a medication inventory status. The medication delivery station can include a housing having a receptacle with the medication closure container disposed in the receptacle, a second communication interface coupled to the housing and in communication with the first communication interface, and a processor and a memory in communication with the processor. In one implementation, the memory include instructions executable by the processor to communicate with the medication closure container via the second communication interface and the first communication interface, receive the container-specific identifier, the medication-specific identifier, and the medication inventory status, and confirm the container-specific identifier.

In a further embodiment, the disclosure provides a method of dispensing a medication from a medication storage and closure container. The method comprises providing the medication closure container with a pill aperture being vacant; forcing the plurality of pills in a silo in a first direction towards an end frame, abutting a first pill of the column against a rotatable end frame with the force, rotating the rotatable end frame, and as the vacant pill aperture of the rotatable end frame rotates past the silo, forcing the first pill of the column into the pill aperture thereby filling the pill aperture with the first pill. The method also includes rotating the rotatable end frame with the first pill in the pill aperture, and as the first pill rotates past an ejection aperture, dispensing the first pill from the container thereby vacating the pill aperture.

In a yet further embodiment, the disclosure provides a method of operating a medication management system comprising a replaceable pre-filled oral solid medication storage and closure container including a plurality of pills, and a medication delivery station including a housing having a receptacle with the medication closure container disposed in the receptacle. The method includes the station communicating with the medication closure container; the station receiving, from the medication closure container, a container-specific identifier, a medication-specific identifier, and a medication inventory status; the station storing, the container-specific identifier, the medication-specific identifier, and the medication inventory status; comparing the container-specific identifier with the expected container-specific identifier; and confirming a correct medication closure container is placed in the receptacle based on the comparison.

In another embodiment, the disclosure provides an automated and adaptable remote management system. The system comprises a replaceable, tamper-poof pre-filled oral solid medication storage and closure container comprising a sealed housing, a medication delivery station comprising a housing having a receptacle with the medication closure container disposed in the receptacle, a user-controlled electronic device in communication with the medication delivery station, and a remote administration portal in communication with the medication delivery station. The system can also include a remote host server in communication with the remote administration portal and in further communication with the medical delivery station. Also discloses is a method for remotely managing and adapting precision dosing the automated and adaptable remote management system.

These and other features and advantages of devices, systems, and methods according to this invention are described in, or are apparent from, the following detailed descriptions of various examples of embodiments, aspects, and constructions.

BRIEF DESCRIPTION OF DRAWINGS

Various examples of embodiments of systems, devices, and methods according to the invention will be described in detail with reference to the following figures.

FIGS. 5A, 5B, and 5C are three perspective views of the medication closure container of the medication closure container of FIG. 2.

FIG. 9A is the medication closure container of FIG. 2 shown in the process of being inserted into the medication delivery station of FIG. 2. FIG. 9B is a top view of the process of FIG. 9A.

FIG. 12A is a perspective view of a portion of the medication delivery station of FIG. 2, the station having a camera visioning system. FIG. 12B is a cutaway vignette of a portion of FIG. 12A.

Figure 1A:
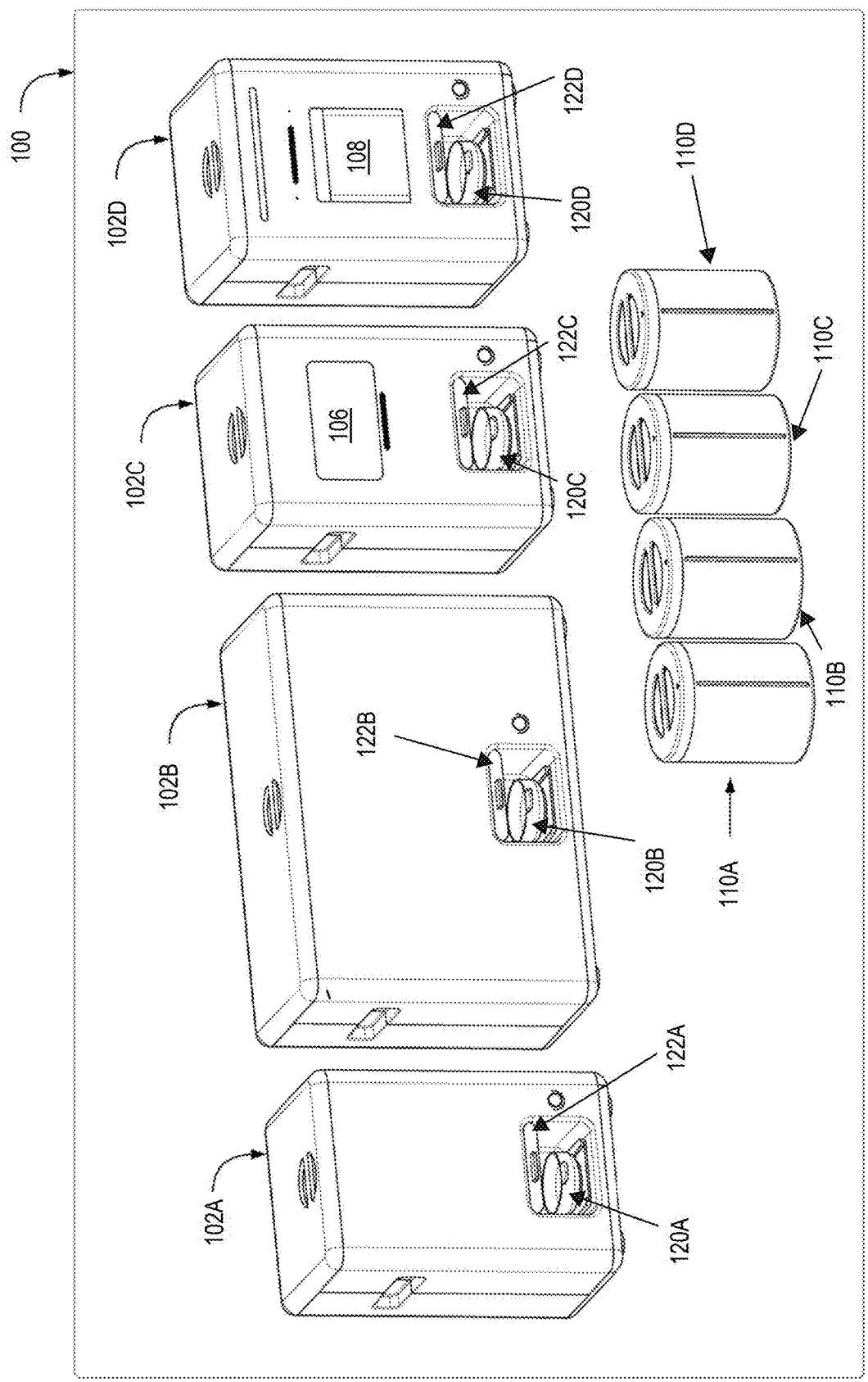
FIG. 1A is a diagram representing a portion of a remote medication management system for automated and adaptive precision dosing.

It should be understood that the drawings are not necessarily to scale. In certain instances, details that are not necessary to the understanding of the invention or render other details difficult to perceive may have been omitted. It should be understood, of course, that the invention is not necessarily limited to the particular embodiments illustrated herein.

Within the scope of this application, it is expressly intended that the various aspects, embodiments, examples, and alternatives set out in the preceding paragraphs, and the claims and/or the following description and drawings, and in particular the individual features thereof, may be taken independently or in any combination. That is, all embodiments and all features of any embodiment can be combined in any way and/or combination, unless such features are incompatible. The applicant reserves the right to change any originally filed claim or file any new claim accordingly, including the right to amend any originally filed claim to depend from and/or incorporate any feature of any other claim although not originally claimed in that manner.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the specific goals of the developer, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Referring to the figures, one or more examples of an automated and adaptable remote medication management system, a mechanism by which the medication management system operates, and a method of operation of the medication management system are shown. The figures illustrate a remote medication management system with replaceable pre-filled medication closure containers stored and under the control of a medication delivery station. In at least one implementation, the medication closure container contains a single medication having a plurality of doses. In one or more constructions, the medication management system is able to identify and count the number of pills or other medication delivered by the delivery station. The medication, or pill, is delivered according to a mechanical and electronic metering system inside the automated remote medication delivery station that holds the pre-filled medication closure container. The medication management system is able to determine the use of medication and may be used to communicate and control the amount used to a user, which may be a patient, a clinician, a caregiver, among other users. By controlling the use and amount of medication delivered through the remote system, patients can achieve more precise dosing therapeutic monitoring and clinicians can adjust in real-time the dosing regimen of a patient to achieve an improved therapeutic response. In addition, the medication management system may be equipped to send a signal to a cell phone or other portable computing device that communicates with a mobile application. In one or more examples, the pre-filled medication closure container is replaceable. In alternative examples, the closure container is refillable.

Embodiments of the disclosure can provide one or more advantages over existing methods for prescribing an individual dosing regimen. The one or more advantages can include, without limitation, (a) safe, tamper-proof, and accurate medication delivery to the user in the home or remote care setting that enables strict medication adherence and reduces the likelihood of medication errors, (b) real-time and accurate reporting medication adherence by the user including the specific dose and timing of the dosing events to better inform the clinician of the need for dosing adjustments, (c) safe, secure, and accurate communication of dosing adjustments to reduce user confusion and medication errors while improving clinical outcomes, and (d) enabling clinical practice infrastructure for treatment decisions at an individual level while reducing the need for office visits and unnecessary healthcare utilization.

Figure 1B:
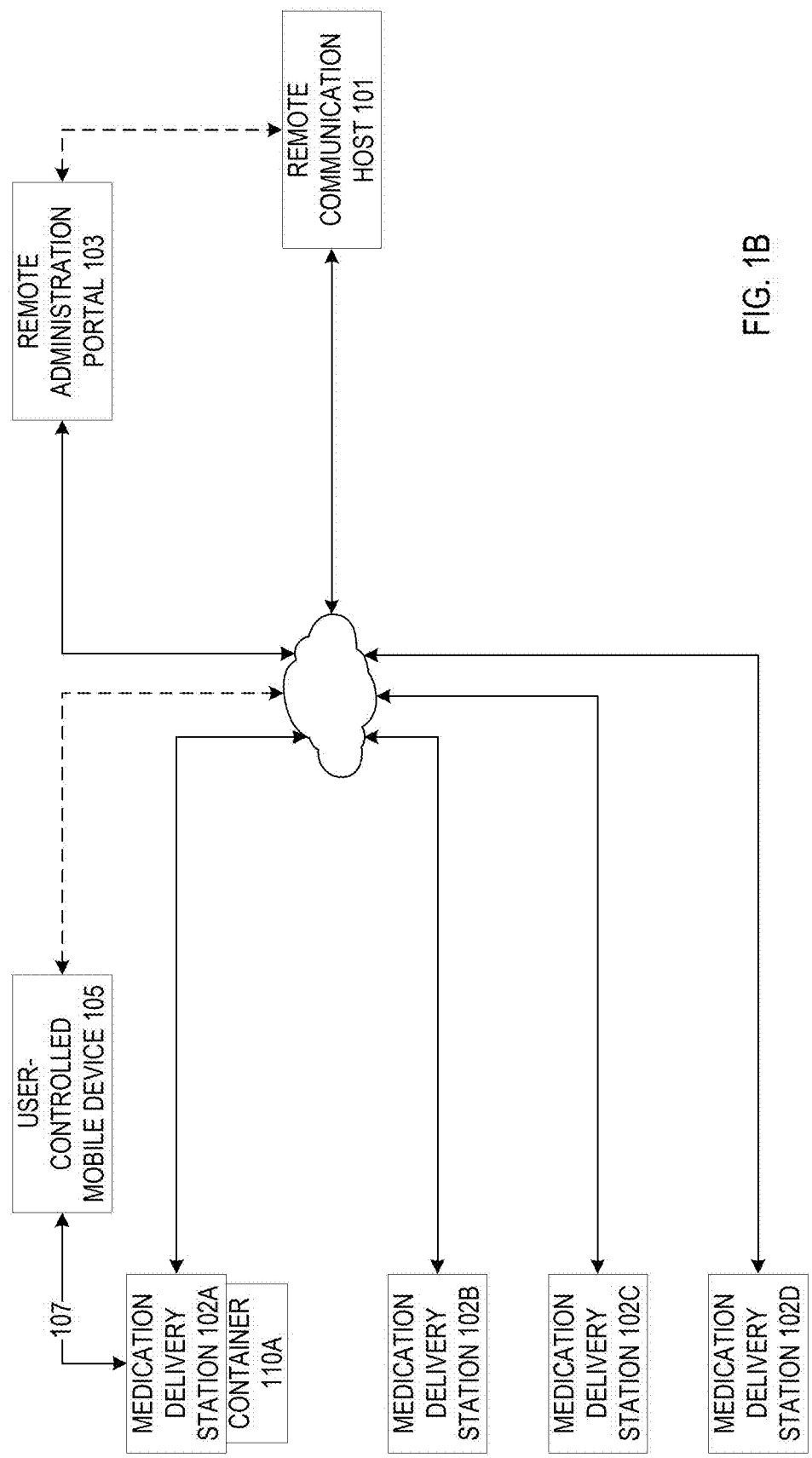
FIG. 1B is a block diagram representing a portion of the remote medication management system of FIG. 1A.

FIGS. 1A-B show a portion of an automated and adaptable remote medication management system 100. The remote medication management system 100 includes medication delivery stations 102A-102D with one or more station container receptacles 104 (shown in FIG. 2) and pre-filled medication closure containers 110A-D. The containers 110A-D are to be inserted into the station container receptacles 104. In FIG. 1, a single medication station 102A and a three-medication station 102B are depicted. FIG. 1 also includes examples a station 102C including an LCD screen 106, and a station 102D having a prescription label pouch 108. The medication delivery stations 102A-102D are communicatively coupled with a remote communication host 101 and a remote administration device 103 via a network. The communication host 101 includes administration software in the form of modules. The remote administration device 103 can include an administrator-controlled portal in communication with the remote communication host 101. An example administrator-controlled electronic portal can be, without limitation, a smart phone, a smart tablet, a web device, a laptop computer, a desktop computer, and many other similar devices. FIG. 1 also shows a user-controlled mobile electronic device 105. The medication delivery stations 102A-102D may be directly connected to the user-controlled electronic device 105 via a wireless connection 107 and/or via the communication host 101.

For example, the medication delivery station 102 can communicate with the communication host 101 which houses one or more of the functions of the medication delivery stations 102A-D. In one or more examples, the medication delivery station 102 and communication host 101 each have a means to receive and transmit a wireless signal. In this regard, the stations 102A-D and/or communication host 101 are provided with a wireless adapter or like component and may connect to a wireless network. In one or more examples, the medication delivery station 102 can include a near field communication device and/or a far field communication. The near field communication device may be used alone or in combination with Bluetooth or Wi-Fi. The far field communication device may be used alone or in combination cellular or satellite communication. Encryption and verification may also be provided, regardless of the form of wireless communication. While wireless communication is described herein, including specific examples, variations thereon would not depart from the overall scope of the present system including, for example, wired communications.

In one construction, the medication delivery station includes four onboard subassemblies. The onboard components may include, but are not limited to, one or more container receptacles, a delivery station drive and control mechanism, communication interfaces, and a medication system with image and weight-based verification. In one construction, the pre-filled medication storage and closure container includes a medication storage module, a drive interface, and a communication interface with the medication delivery station. The medication storage and closure container stores medications in silo columns and releases the medications under the direction of the delivery station drive and control mechanism. Further examples regarding the medication delivery station and pre-filled medication storage and closure container are described below.

In one construction, an automated remote medication management system for precision dosing contains all the hardware and localized control systems required to perform independent medication release operations. Functions are further enhanced by the communication and control application which may reside on a third-party host. In one or more embodiments, the medication delivery station operates independently of the mobile application.

Figure 2:
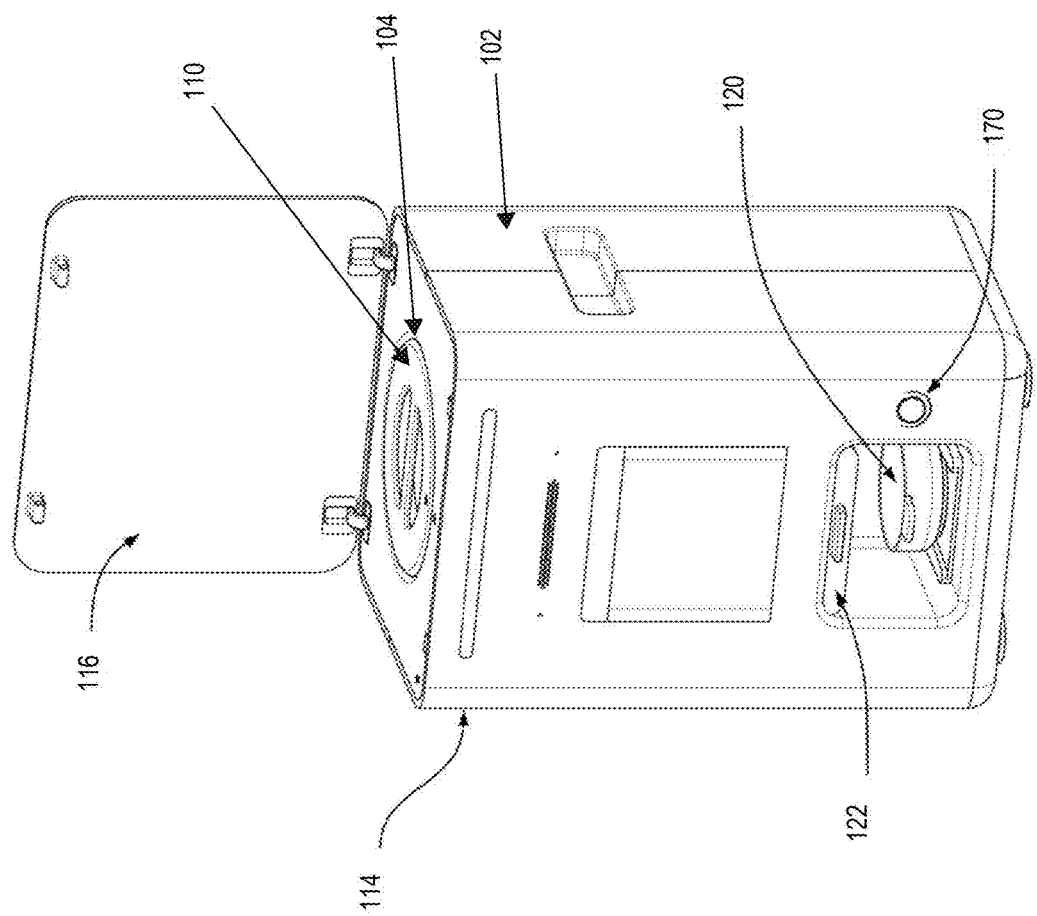
FIG. 2 is a perspective view of a medication delivery station used in the system of FIG. 1, the station having a replaceable pre-filled medication storage and closure container.

FIG. 2 illustrates the medication delivery station 102A (hereinafter simply referred to as 102) of FIG. 1 having a replaceable pre-filled medication storage and closure container 110A (hereinafter simply referred to as 110). The medication delivery station 102 includes a station housing 114 and a station container receptacle 104 for the proper placement of the medication closure container 110 into the medication delivery station 102. The medication of the medication closure container 110 is delivered into a removable medication receptacle 120, which can be behind a slidable door 122. A delivery station lid 116 opens and shuts to allow a user (e.g., a patient, pharmacist, caregiver, nurse, medical practitioner) to remove and replace the medication closure container 110. A more detailed description of the medication delivery station 102 and the medication closure container 110 is provided below.

Figure 3:
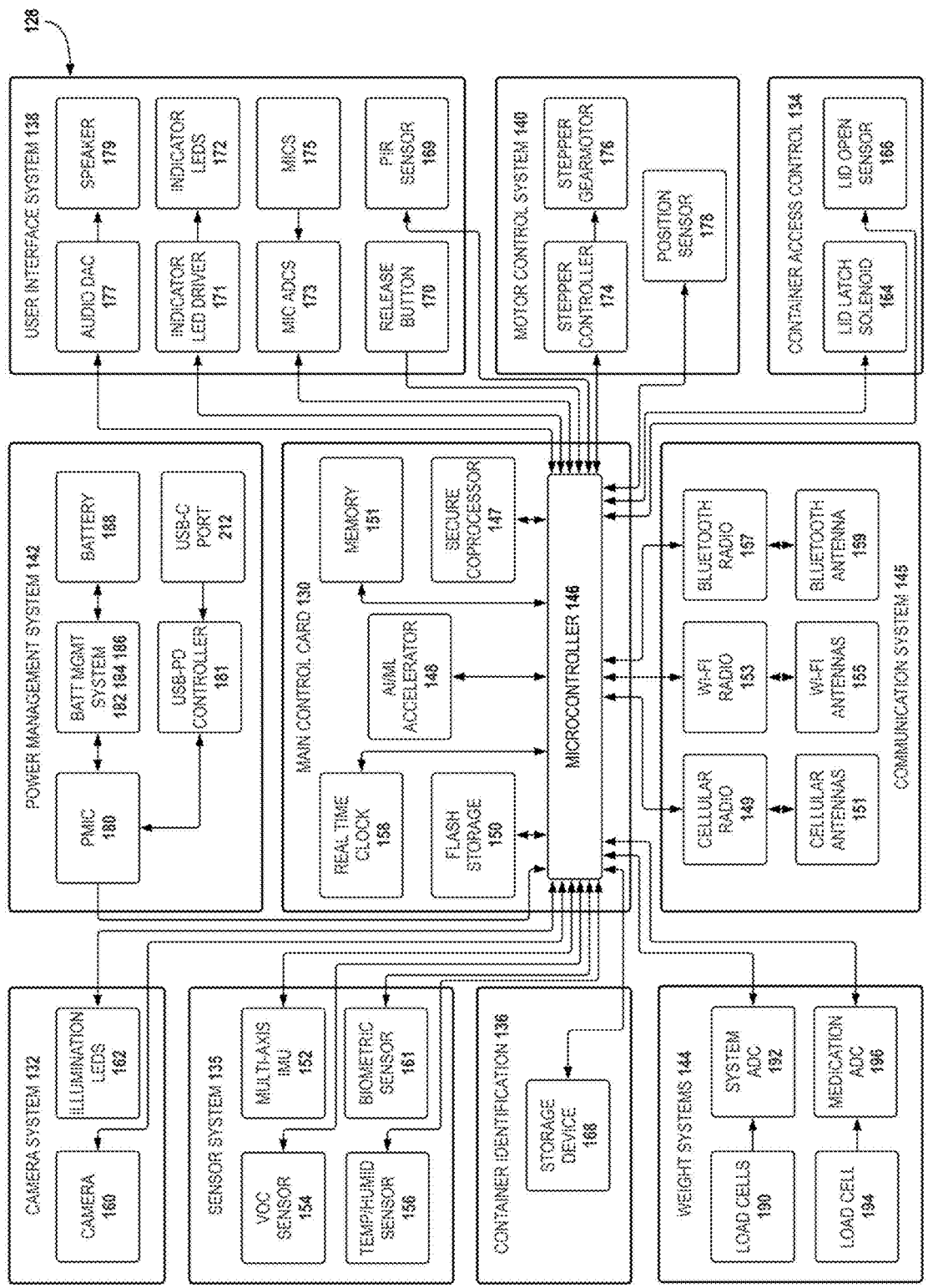
FIG. 3 is a schema of a delivery station system architecture for the medication delivery station of FIG. 2.
Figure 4:
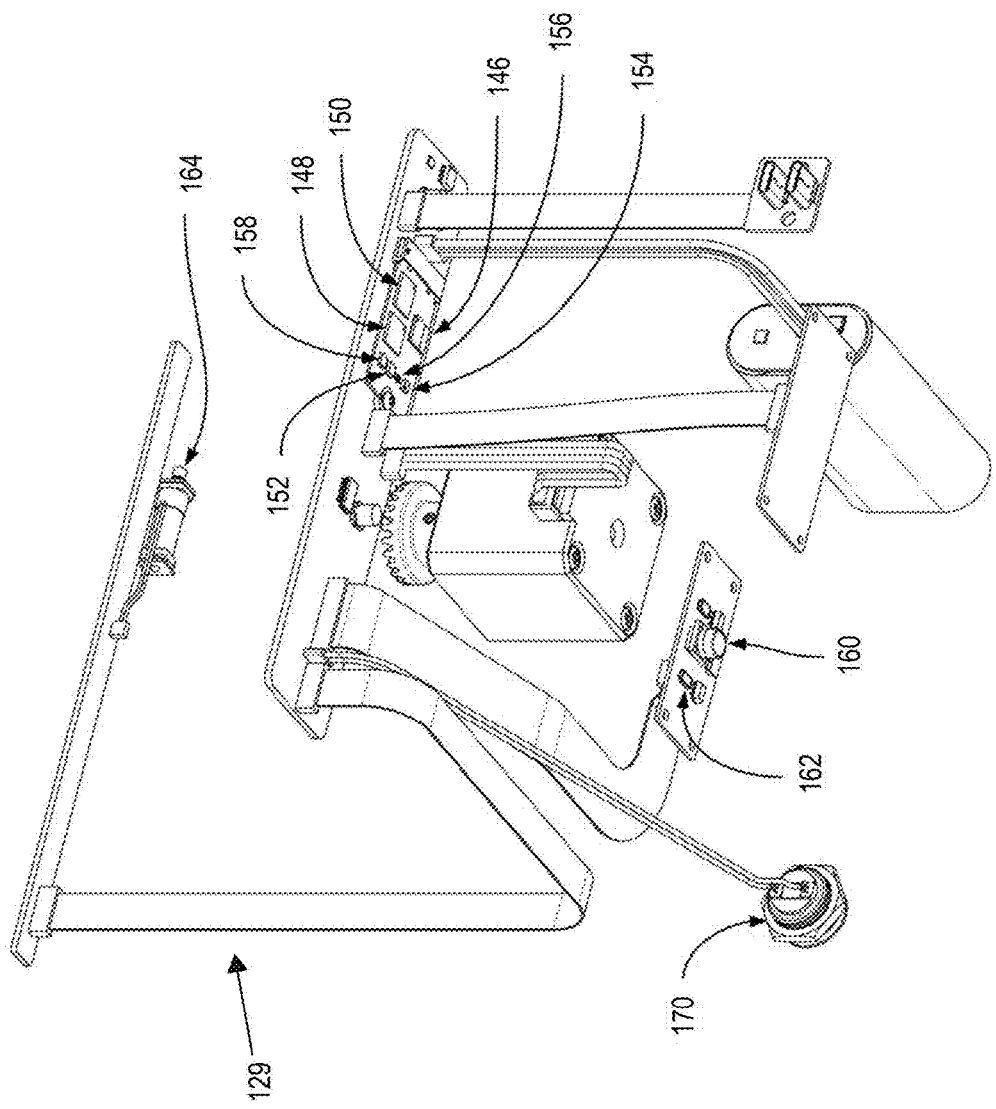
FIG. 4 is a cut-away perspective view of the electrical system of the medication delivery station of FIG. 2.
Figure 5C:
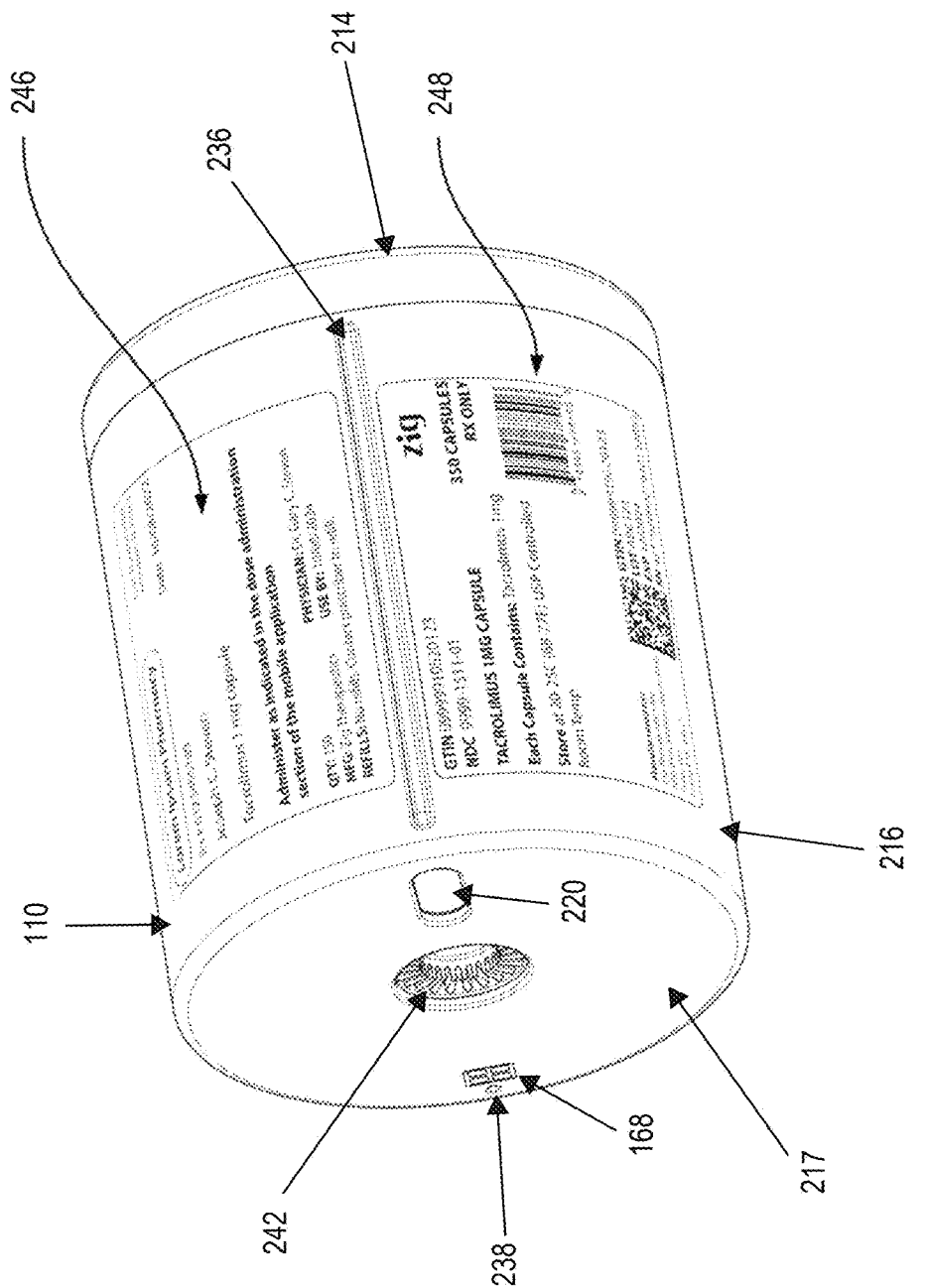

FIG. 3 provides a schema of a delivery station system architecture 128 of the medication delivery station 102. FIG. 4 illustrates a portion of an electrical system 129 of the medication delivery station 102. A main control card 130 contains a microcontroller 146 which provides computation, sensor interfaces, and communication interfaces for the device. The communication system 145 can contain a cellular radio 149 with cellular antennas 151, a Wi-Fi radio 153 with Wi-Fi antennas 155 and a Bluetooth radio 157 with Bluetooth antenna 159, or any combination thereof. The microcontroller 146 has a connection to a real-time clock 158 to provide accuracy in timekeeping and calendaring for dosing window activation and a connection to flash storage 150 for data retention. In some implementations, the microcontroller 146 uses a secure coprocessor 147 for cryptographic processing and secure key storage. The microcontroller 146 has electrical connections to a sensor system 135 containing a multi-axis inertia measurement unit (IMU) 152 to detect movement and vibration, a volatile organic compounds (VOC) sensor 154 to detect gases that may have inadvertently entered the medication delivery station 102, and a temperature and humidity sensor 156 to measure the temperature and humidity inside the station 102. In some embodiments, the sensor system 135 contains a biometric sensor 161 for secure authentication prior to device use. A second microcontroller 148 with artificial intelligence and neural network acceleration communicates with the camera and illumination system 132 for automated image-based processing. In some embodiments, the artificial intelligence microcontroller 148 is implemented as a neural network accelerator connected to the primary microcontroller 146. The camera and illumination system 132 contains a visible light camera 160 and LED illumination 162 with LED drivers for control of illumination. In some embodiments the camera 160 is also sensitive to infrared illumination from infrared LEDs 162. In other embodiments, a plurality of cameras performs imaging functions. The camera and illumination system 132 acquires an image of a pill released from the container. The camera and illumination system 132 can perform automated detection to count the number of pills released during a dosing event and to determine if the pill has been broken or destroyed and should not be administered to the patient.

The microcontrollers 146 and 148 each include a processor and memory. It is contemplated that the processors and memories may each be a single electronic device or formed from multiple devices. The processors can include a component or group of components that are configured to execute, implement, and/or perform any of the processes or functions described herein for the device it is part of or a form of instructions to carry out such processes or cause such processes to be performed. Examples of suitable processors include a microprocessor, a microcontroller including a processor, and other circuitry that can execute software. Further examples of suitable processors, which can be part of or alternative to the microcontrollers, include, but are not limited to, a core processor, a central processing unit (CPU), a graphical processing unit (GPU), an array processor, a vector processor, a digital signal processor (DSP), a field-programmable gate array (FPGA), a programmable logic array (PLA), an application specific integrated circuit (ASIC), math co-processors, and programmable logic circuitry. The processor can include a hardware circuit (e.g., an integrated circuit) configured to carry out instructions contained in program code. In arrangements in which there are a plurality of processors, such processors can work independently from each other, or one or more processors can work in combination with each other.

A memory includes memory for storing one or more types of instructions, information, and/or data. The memory can include volatile and/or non-volatile memory. Examples of suitable memory include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, disks, drives, or any other suitable storage medium, or any combination thereof. The memory can be a component of a processor (or the microcontrollers), can be operatively connected to the processor (or microcontrollers) for use thereby, or a combination of both.

In one or more arrangements, the memory can include data and various instructions stored thereon. For example, the memory can store instructions in the form of one or more modules. Modules can be or include computer-readable instructions that, when executed by the processor, cause the processor to perform the various functions disclosed for the module. While functions may be described herein for purposes of brevity, it is noted that the functions for the device are performed by the processor using the instructions stored on or included in the various modules. Some modules may be stored remotely and accessible by the processor using, for instance, various communication devices and protocols. One or more programs or modules may be stored in the memory for execution by the processor.

The container access control system 134 electrically couples to the microcontroller 146. The container access control system 134 determines if the delivery station lid 116 (FIG. 2) is open or shut using a sensor 166. The sensor 166 can be an ambient light sensor, a mechanical switch, a hall effect sensor with an embedded magnet in the station lid 116, or a similar sensor. The microcontroller 146 actuates a lid latch solenoid 164 to allow access to open the lid 116 when a change of the medical closure container 110 is required and authorized. Also electronically coupled to the microcontroller 146 on the main control card 130 is the container identification system 136. The container identification system 136 authenticates the pairing of the container storage and communication chip 168 (FIG. 3) with the medication delivery station 102. The container identification system 136 can be based on unique container identifiers and a remote administrator communication of a dosing regimen for the patient including the medication-specific closure container identifier.

In at least one implementation, the user interface system 138 can include a release button 170 which the patient depresses at the time of the dosing event. The release button initiates a signal to the microcontroller 146 to activate the motor control and feedback system 140 to release the prescribed and scheduled medication dose into the medication receptacle 120. In some embodiments, a proximity sensor 169 is used to determine the presence of a user near the station 102. During the insertion of the medication closure container 110 into the station 102, the container status LED indicator 172 electronically coupled to the microcontroller 146 changes from red to green to signal successful placement into the station container receptacle 104. For color blind individuals, the container status LED indicator 172 instead uses flashing and solid indicator patterns rather than colored lighting for user feedback. In some embodiments, an additional visual status LED indicator 172 using a single colored or flashing light (e.g. red-green-blue (RGB) light emitting diode (LED)) or a plurality of colored or flashing lights provides additional visual feedback to the user during interaction with the device. Such LED indicators are coupled to the microcontroller 146 via a LED driver 171. Some implementations include audio devices in the user interface system 138. In these implementations, an audio digital to analog converter (DAC) 177 is connected to a speaker 179 to provide audio output while microphones 175 are connected to analog to digital converters (ADCs) 173 to provide audio input.

The motor control and feedback system 140 is electronically coupled to the microcontroller 146. The motor control and feedback system 140 includes a stepper motor 176, a stepper motor controller 174, and a position optical sensor 178 that interfaces with the microcontroller 146. The microcontroller 146 controls the motor control and feedback system 140 to release the appropriate dose at the scheduled dosing event time and verify the position of rotary components within the container closure during release. In some constructions, the stepper motor 176 features an attached gearbox to modify the motor output while in other constructions, the stepper motor 176 is replaced with an alternate motor type such as a servo motor. In some implementations, the optical sensor is replaced by a mechanical limit switch with actuating features on the rotating inner plate of the container, or a hall effect sensor with magnets embedded in the rotating inner plate of the container. In other embodiments, positional feedback is received from an optical or hall effect rotary encoder on the motor output shaft.

The power management system 142 includes a primary power management integrated circuit (PMIC) 180, a battery management system (BMS) having a charge controller 182, protection circuitry 184, and a fuel gauge 186, and a backup battery 188. The PMIC is electronically connected to the microcontroller 146 on the main control card 130 for system power management. Power is input to the station 102 using a power connector 212. In some embodiments, the power connector 212 is a USB-C type connector which is attached to a USB power delivery (PD) controller 181. In other embodiments, an alternate power connector is used, such as a DC barrel jack.

The weight systems 144 use load cells 190 and 194 to measure the system weight and the weight of the medication receptacle 120 to document the release of the scheduled medication into the receptacle 120. The medication receptacle load cell 194 weight system provides a tare weight of the medication receptacle 120 prior to dose release. The medication receptacle load cell 194 validates weight of pills released using reference data from the container identification system 136 and one or more reference libraries stored by the microcontroller 146 on the main control card 130 or in remote software. The medication receptacle load cell 194 in concert with the microcontroller 146 verifies that the number of pills scheduled for the dosing event have been released into the medication receptacle 120.

The station load cell 190 measurements assist in the identification of whether the medication closure container 110 has been inserted into or removed from the station 102. The station load cells 190 weight measurements are coupled with input from the IMU 152 to determine patterns of device interaction that could be the result of a tamper attempt. The medication receptacle load cell 194 and station load cells 190 are connected to high-resolution analog to digital converters 192 and 196, which communicate with the microcontroller 146 on the main control card 130.

Before moving to other components, it should be understood by somebody skilled in the art that the electrical and electronic devices discussed herein include additional conventional elements typically found in electrical and electronic devices. Further discussion regarding these components is not provided herein since the components are conventional and their operation is conventional.

Referring to FIGS. 5-8, the pre-filled medication storage and closure container 110 contains a pre-loaded quantity of medication sealed and stored in a silo configuration. The shown medication in the figures is an oral solid medication, such a plurality of pills. According to one or more implementations, the internal components of the medication closure container 110 are sized to accept and contain the pills 112 to be released. The medication closure container 110 contains a housing having a housing component 216 and a housing cover 214 providing the pill silo storage volume 215. The housing component 216 has three alignment rails 236 that navigate the insertion of the medication closure container 110 into the station container receptacle 104. The housing cover 214 has a user installation handle 218 is bonded to the top of the housing component 216 for the container 110. On the first housing cover 214 is a container alignment pictogram 240. The pictogram 240 is aligned to the corresponding container status LED indicator 172 on the top surface of the medication delivery station 102 to signal proper alignment and placement of the medication closure container 110 into the station container receptacle 104. The housing component 216 includes an end 217 that provides a container drive system interface 242. The interface 242 connects with a station drive interface 208 (FIG. 10) and the container pill release aperture 220 through which the pills 112 are released. The medication closure container 110 includes a storage and communication chip 168 that includes pill identification, container-specific code, write-back inventory status, and a source-of-truth fallback on the dose schedule. The medication closure container 110 includes an alignment witness hole 238 through which reference features on the rotating inner plate 230 (FIG. 7) are detected by an optical sensor 178 (FIG. 178) to detect positional changes during medication release.

Before proceeding further, it is noted that the number of housing components and the shape of the housing can vary from what is shown. For example, the exterior shape of the shown medication closure container 110 is substantially cylindrical having first and second circular ends with a single side wall. However, other shapes are envisioned. Also, the shown housing of the medication closure container 110 includes two portions: lower housing component 216 and housing cover 214. However, the number of housing portions can vary, such as two end covers and a single side wall.

To prescribe the pre-filled medication closure container 110 to a specific user (such as a patient) a medical practitioner (such as a pharmacist) adheres a human-readable prescription label 246 to the container 110. Additionally or alternatively, the medical practitioner can also include the prescription label 246 in a pouch 108 (FIG. 1) on the front of the medication delivery station 102D. Bar codes 248 can also be included by the manufacturer to provide machine-readable device and medication information that can be scanned by the medical practitioner upon dispensing the medication closure container 110 to a user.

Figure 7:
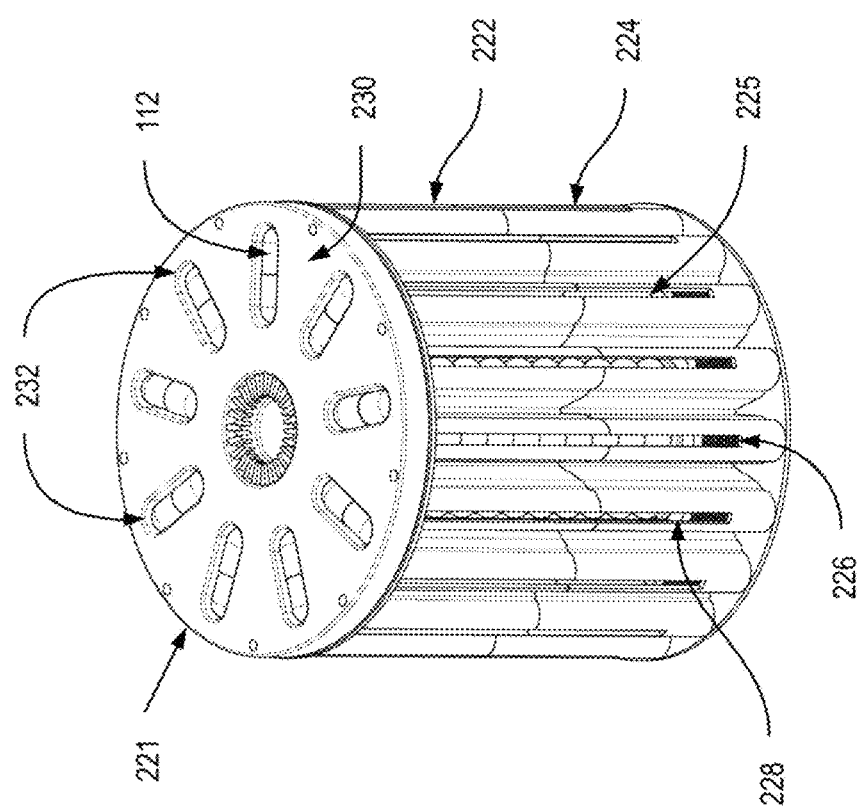
FIG. 7 is a perspective view of a cut-away inverted medication closure container of the medication closure container of FIGS. 5A-5C.
Figure 6:
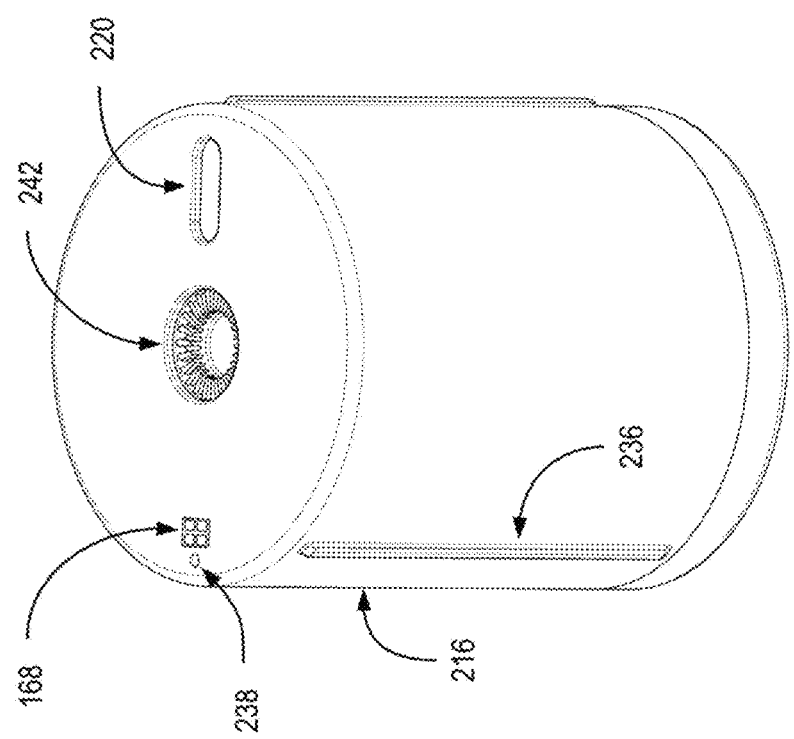
FIG. 6 is a perspective view of a housing component of the medication closure container of FIGS. 5A-5C.
Figure 8A:
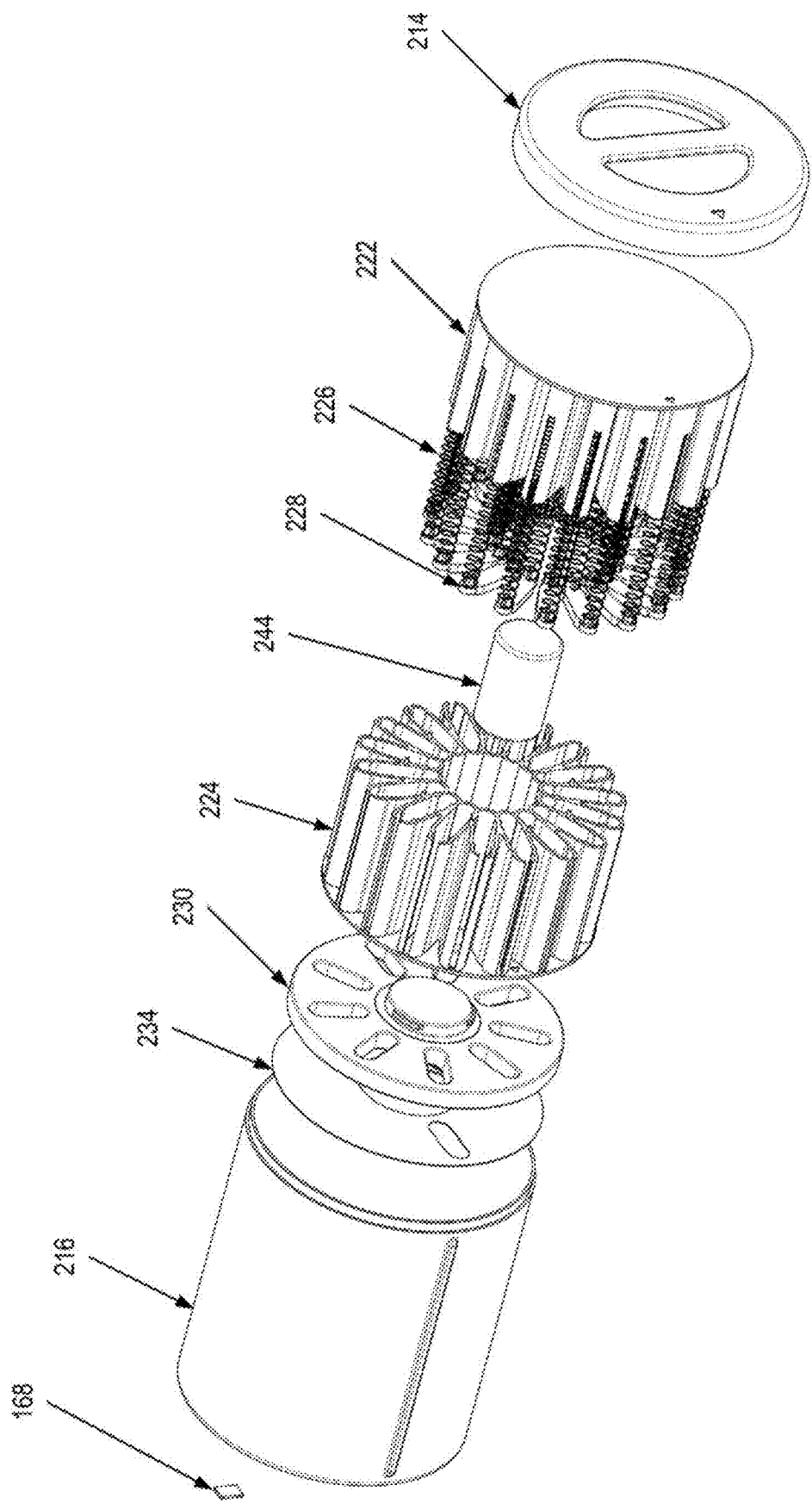
FIG. 8A is an exploded view of the medication closure container of FIGS. 5A-5C.
Figure 8B:
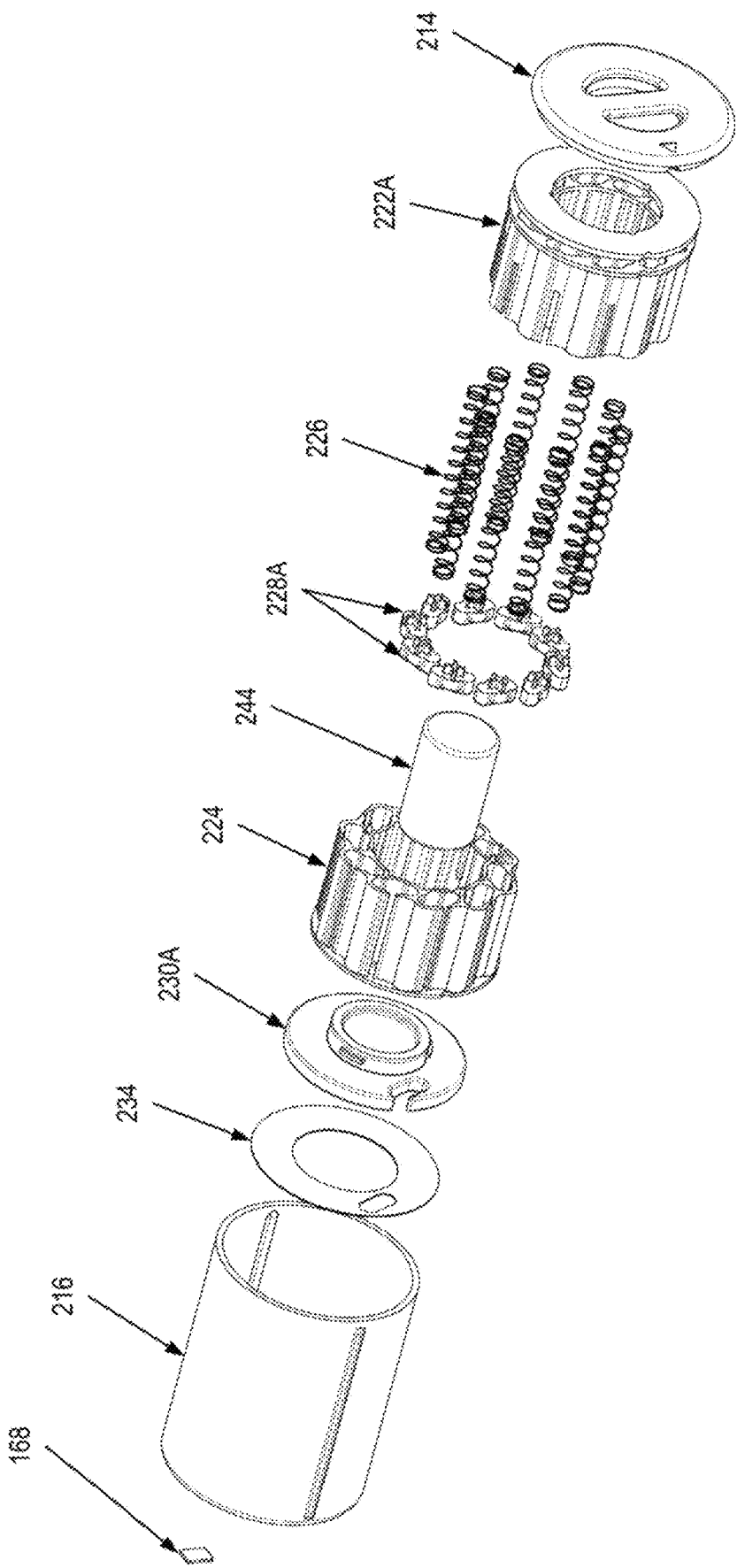
FIG. 8B is an exploded view of a second medication closure container capable of being used with the system of FIG. 1.

As illustrated in FIGS. 6-8, an internal lattice pill storage cartridge 221 includes a lower pill storage cartridge 224 and an upper pill storage cartridge 222 that are bonded together. The lattice pill storage cartridge 221 stores the pre-determined quantity of pills 112, and the container housing encloses the combined cartridge 221 in the volume 215. In one or more examples, one or more compression springs 226 seated on a spring cap 228 are located within the storage cartridge 221. As a result, spring pressure is exerted between the upper aspect of each pill silo (e.g. silo 225) and the column of pills in the direction of the inner plate 230. Spring force (assisted by gravity) is provided to insert a dose of medication into a vacant cavity or aperture 232 in the inner plate 230. Once an aperture or cavity is populated, the resident medication or pill 112 serves as a stop which inhibits additional silos from loading into that particular aperture or cavity 232. To absorb moisture, a desiccant cartridge 244 is placed in the center of the container, and a foam seal 234 prevents water or dust ingress from the interface area on the lower aspect of the housing component 216.

Figure 10:
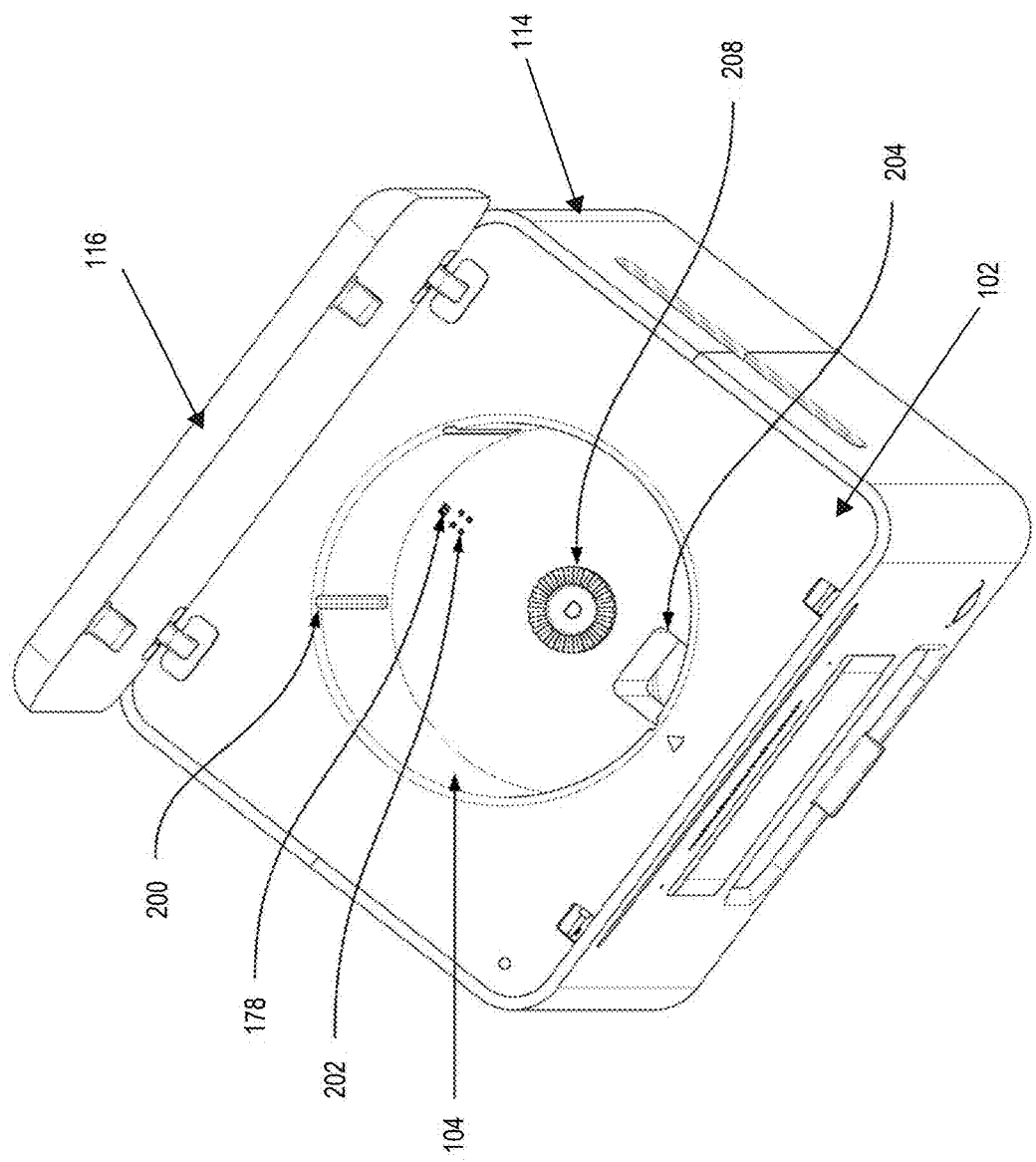
FIG. 10 a top perspective view of the medication delivery station of FIG. 2 in an open state with the medication closure container removed.

Referring to FIGS. 9A, 9B, and 10, the user inserts the medication closure container 110 into the station container receptacle 104 with assistance from the installation handle 218. Each medication closure container 110 is inserted into medication delivery station 102 after aligning the container status LED indicator 172 on the upper surface of the station container receptacle 104 in direct alignment with the container alignment pictogram 240 on the upper surface of the container 110. In addition to the visual feedback, three alignment rails 236 arranged around the periphery of the closure container are inserted into the three alignment rail guides 200. Asymmetry in the alignment rail angular positioning ensures that a medication closure container 110 cannot be inserted incorrectly. The interface area of the medication delivery station 102 includes spring loaded contact pins 202 to communicate identification and inventory information between the closure container storage and communication chip 168 and the microcontroller 146 on the main control card 130, and the alignment rail guides 200 prevent this electrical connection from becoming misaligned. Container status LED indicators 172 inform the patient when the medication closure container 110 is properly inserted based on information received from the container communication chip 168. The connection to the drive interface 208 is self-centering to be tolerant of minor misalignment of the interface 208 and the drive exposure of the inner plate 230. The drive interface 208 with the drive exposure promotes movement of the silo storage cartridge 221. The medication release aperture 220 on the medication closure container 110 aligns with the pill outlet 204 on the medication delivery station 102 into the pill chute 206. An optical sensor 178 aligned with the witness hole 238 on the lower housing component 216 of the container provides feedback on the position of the inner plate 230 of the medication closure container 110 during the release of medication.

Figure 11:
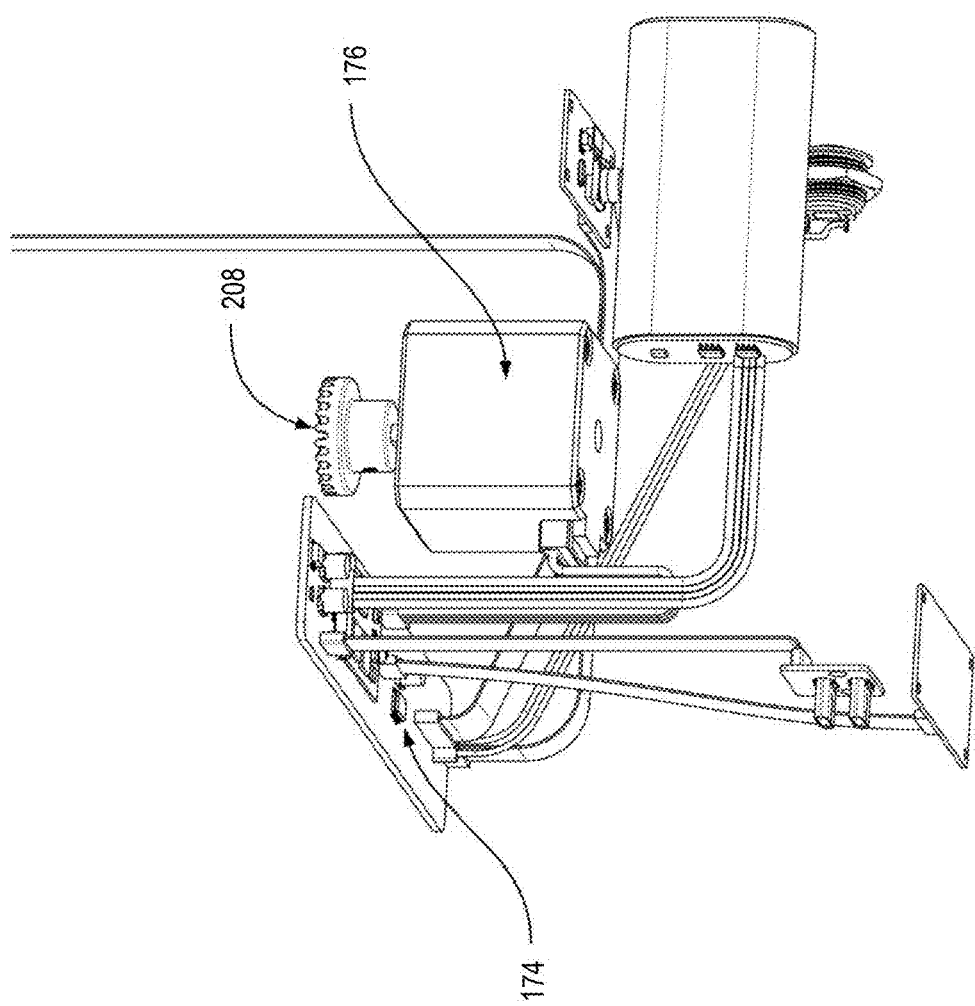
FIG. 11 is a cutaway perspective view of the motor control system of the motor and drive interface system of the medication delivery station of FIG. 2.

Referring to FIG. 11, the station drive interface 208 translates rotary motion from the station stepper motor 176 to the container drive system interface 242 on the inner plate 230 of the medication closure container 110. In some constructions, chamfered or rounded gear-like geometry allows passive angular correction of misalignment between the station drive interface 208 and the container drive system interface 242. In other constructions, the station drive interface 208 or a subsystem including of the station drive interface 208 and stepper motor 176 retract on a spring mechanism during container insertion. Misalignment between the interfaces 208 and 242 is corrected by rotating the stepper motor 176 shaft until mating surfaces align and the spring mechanism approximates the two halves of the interface. In some constructions, the stepper motor 176 turns the station drive interface 208 repetitively in alternating directions to correct minor misalignment between the halves of the interface during the process of container insertion. After the medication closure container 110 is connected, during the next dosing event, precise control of the inner plate 230 rotation is achieved by the microcontroller 146 on the main control card 130 issuing control commands to the station stepper motor control circuitry 174 and receiving feedback from the optical sensor 178. As the inner plate 230 rotates, a pill 112 loaded into an inner plate aperture 232 aligns with the container pill release aperture 220. The pill 112 falls through the station pill outlet 204 through the pill chute 206 and into the medication receptacle 120. Subsequently, the now-vacant cavity 232 in the inner plate 230 continues rotating until aligning with a pill silo 222 and 224 containing medication. The springs 226 can exert force through the spring caps 228 and stack of pills, causing the next pill 112 in the column to populate the inner plate cavity 232. This process repeats in succession until the prescribed number of pills 112 have been released into the medication receptacle 120.

In other embodiments (see FIG. 8B), the inner plate 230A features a solitary aperture which shuttles pills from the storage silos to the pill release aperture using bidirectional rotary motion instead of continuous rotary motion. The stepper motor indexes the inner plate aperture to a pill silo containing medication which populates the aperture with a pill, then subsequently indexes the inner plate aperture to the pill release aperture, at which the pill falls through the station pill outlet through the pill chute and into the medication cup. In each embodiment, motor control parameters including but not limited to starting speed, maximum speed, maximum acceleration, maximum deceleration, acceleration and deceleration relative to rotational motion endpoints, microstepping fraction and other motor control parameters are modulated by software or referenced from stored motion control variables on the main control card for optimal control of pill release, which is actuated by the stepper motor by the stepper motor control circuitry.

Medication is released from the medication delivery station 102 during a pre-approved dosing event defined by the number of pills 112 per dose. Only medication prescribed for the current dosing window is available for release when the release button 170 is pressed by the patient. The mobile application can notify the patient of an upcoming scheduled dosing event at a specific dosing window.

Figure 13:
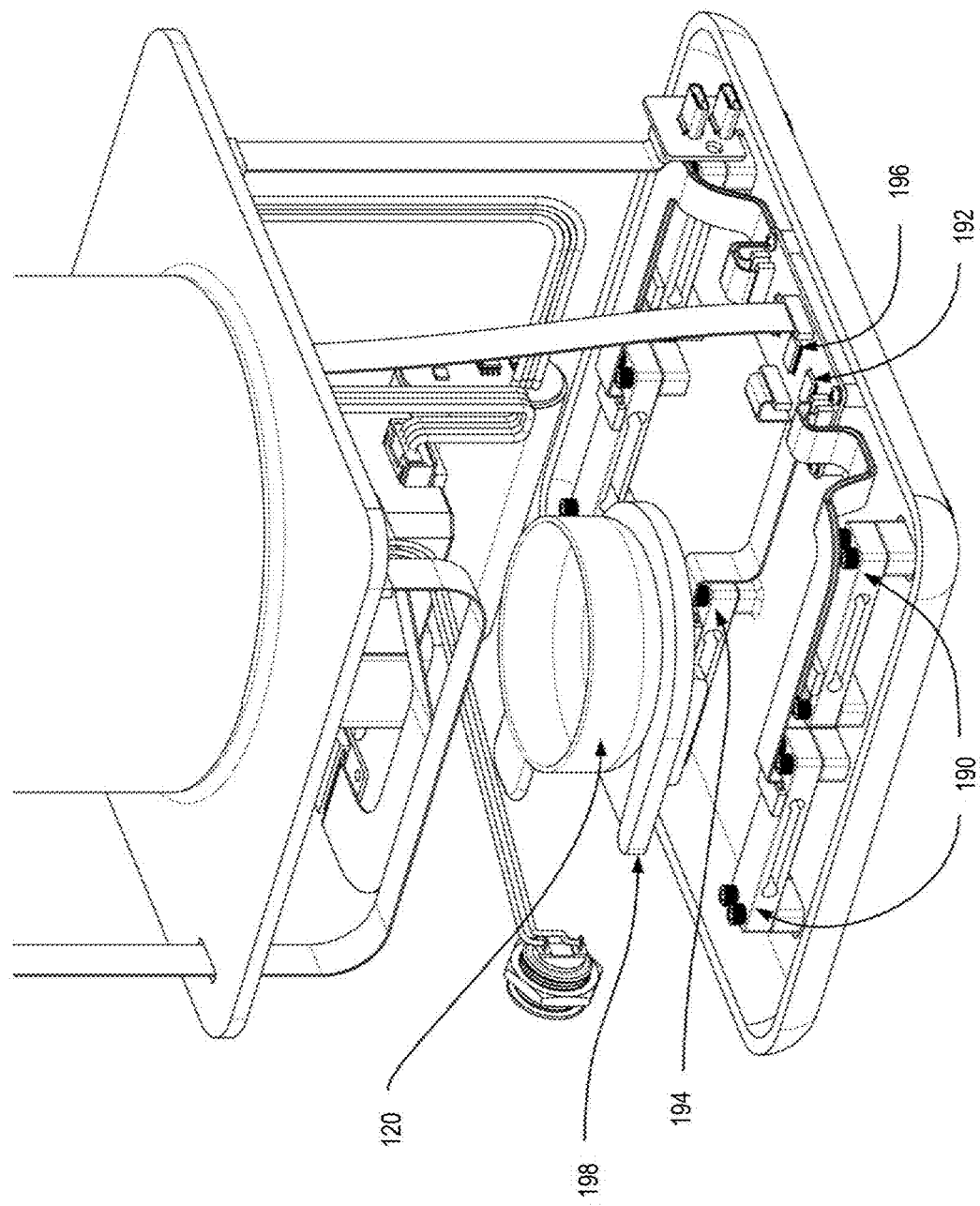
FIG. 13 is a partial cutaway perspective view of the lower assembly of the medication delivery station of FIG. 2, the lower assembly having a weight measurement system.
Figure 14:
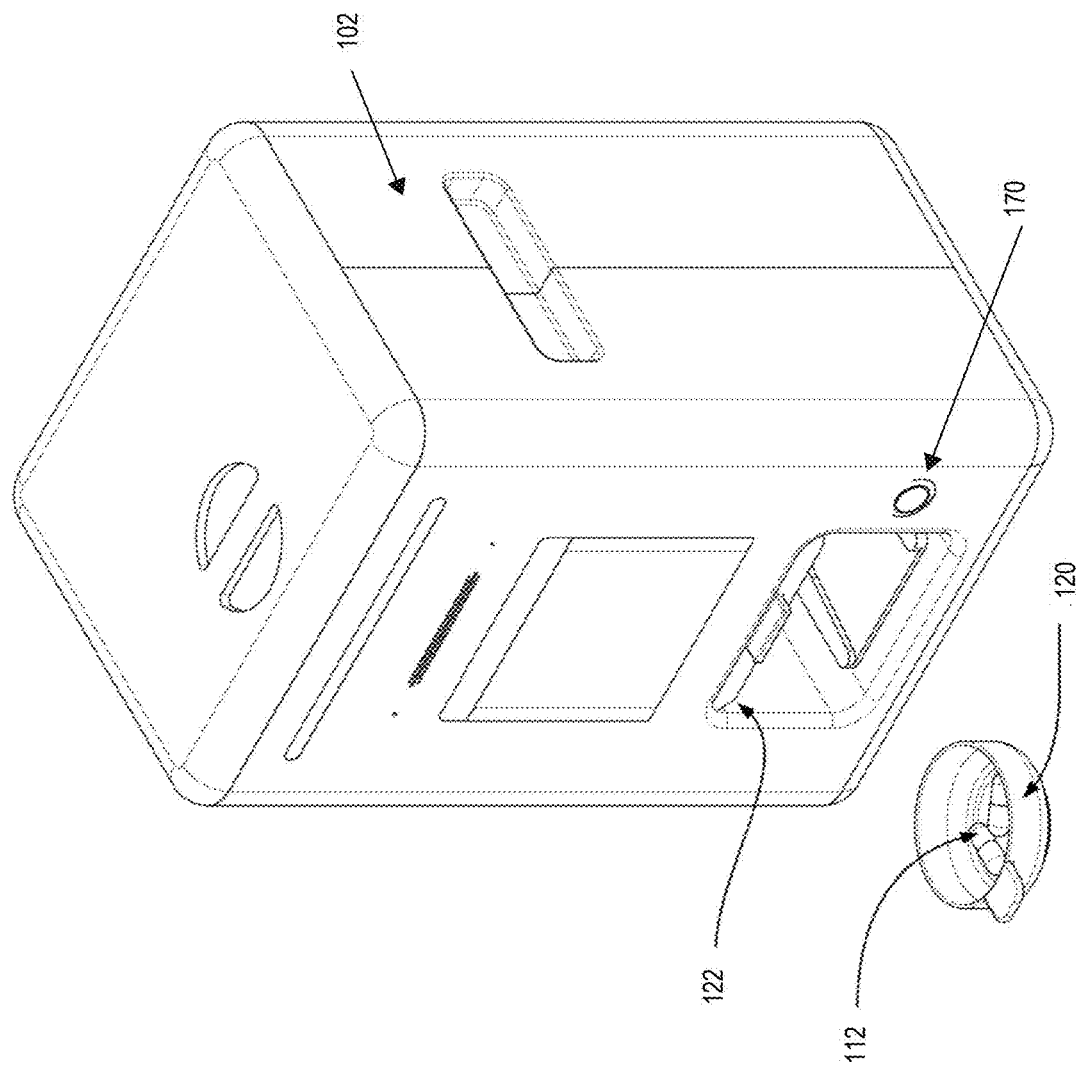
FIG. 14 is a partial perspective view of a medication receptacle removed from the medication delivery station of FIG. 2.

As illustrated in FIGS. 12-14, at the time of a scheduled dose, the user is prompted by the mobile application to press the station release button 170. The released pills 112 fall through the pill chute 206 into the medication receptacle 120 where the released dose is verified by weight on the self-centering weight platform 198. The released pill 112 can further be verified using image analysis with the camera and illumination system 132. The medication receptacle load cell 194 is connected to a high-resolution analog to digital converter (ADC) 196. Prior to the pill 112 release, the station administration software tares the medication scale with the medication receptacle 120 on the self-centering weight platform 198. The station administration software can further use real-time image analysis from the camera and illumination system 132 as an alternate method to verify the medication receptacle 120 is empty and in position. After the medication has been released by the medication delivery station 102, the patient opens the slidable door 122 and removes the medication receptacle 120. When the medication receptacle 120 is removed from the medication receptacle load cell 194, the microcontroller 146 communicates information about this dosing event to the mobile application and to the remote administration portal. The inventory of available pills 112 in the medication closure container 110 is updated on the container storage and communication chip 168, the microcontroller data storage 150, the mobile application, and the remote administration portal. The patient administers the dose, replaces the medication receptacle 120, and closes the slidable door 122 in the station 102.

Figure 15:
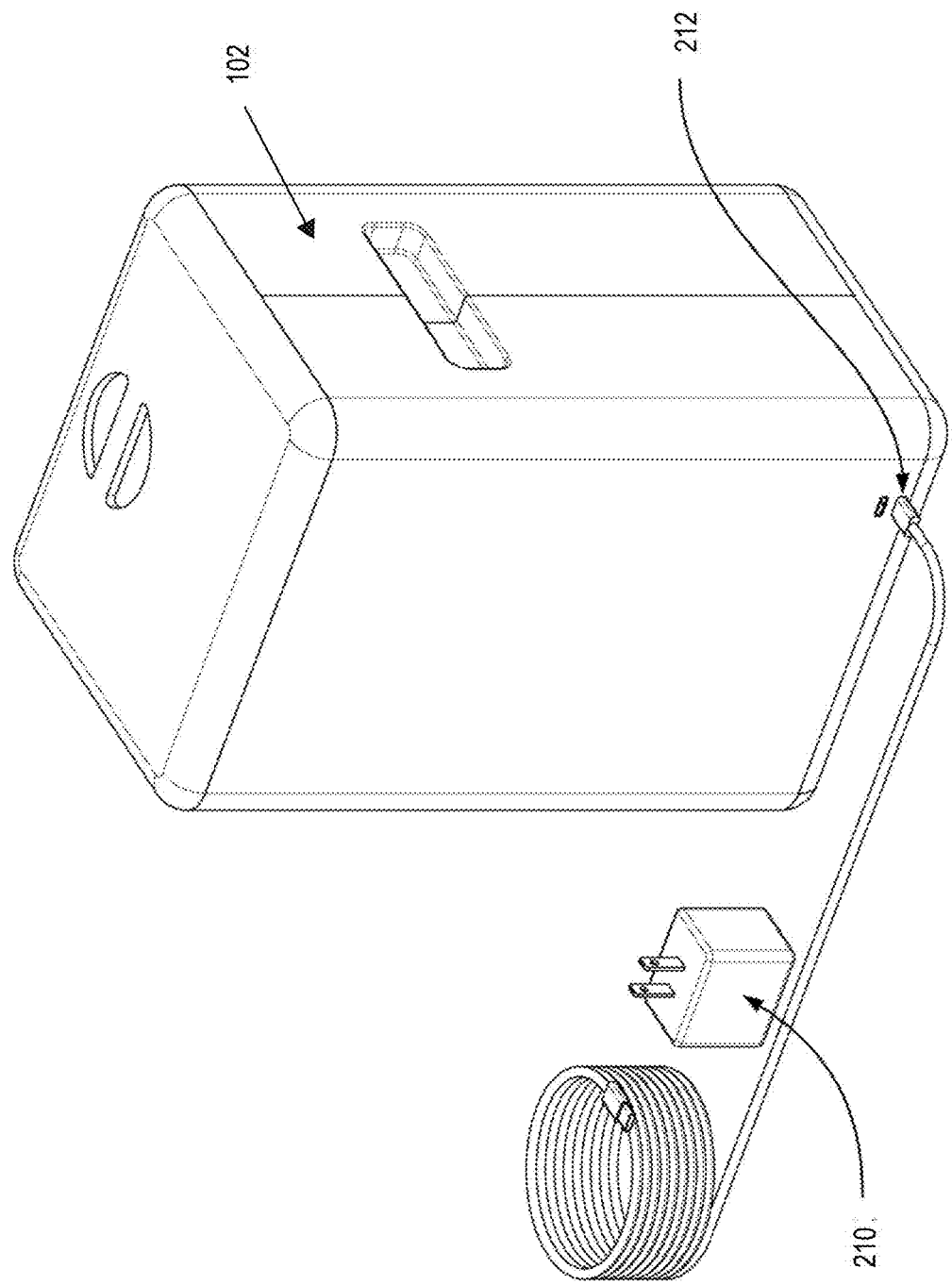
FIG. 15 is a perspective view of the rear of the medication delivery station of FIG. 2 with disconnected external power source.
Figure 16:
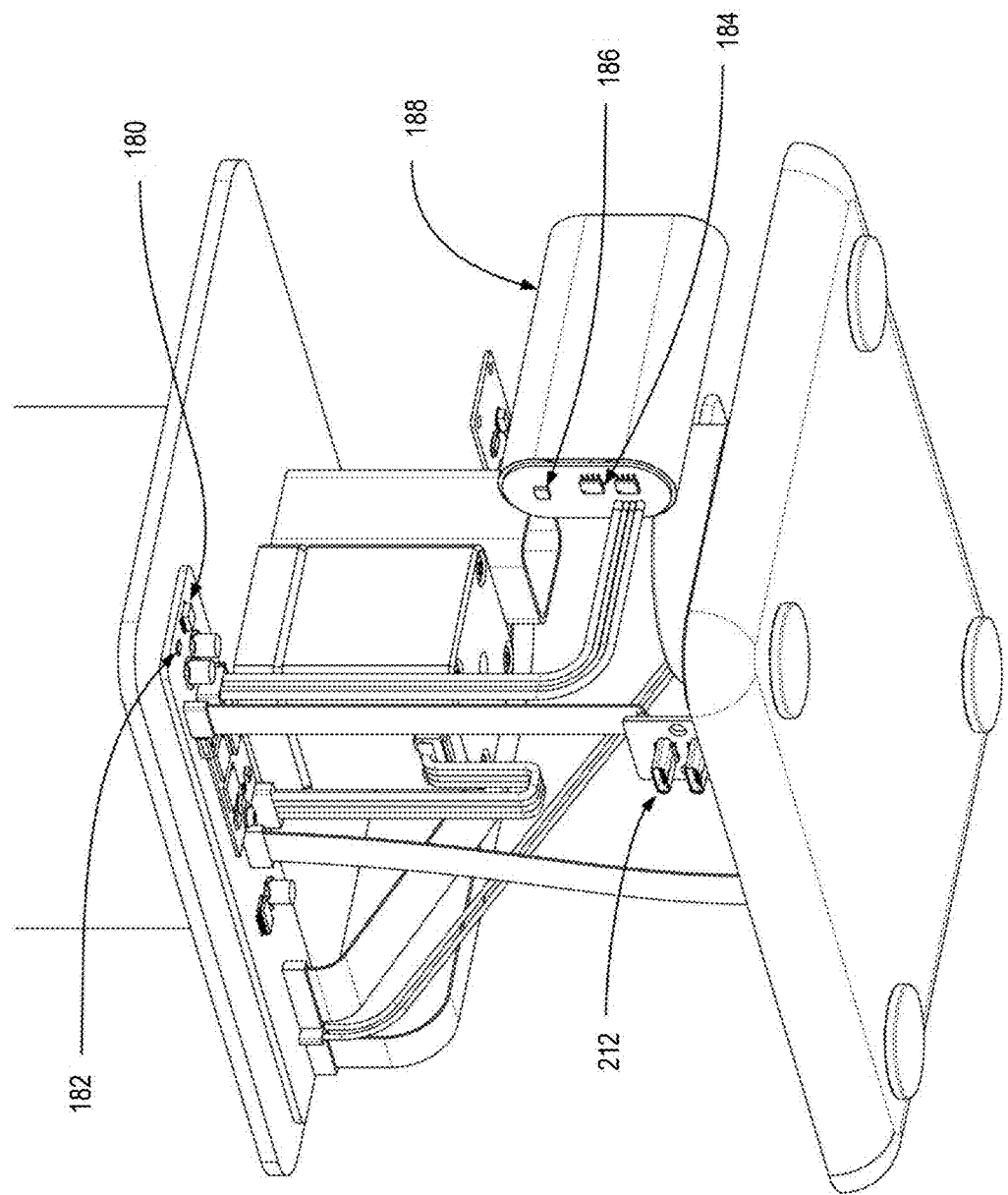
FIG. 16 is an upward perspective view of a cut-away depicting an internal power control systems.
Figure 17E:
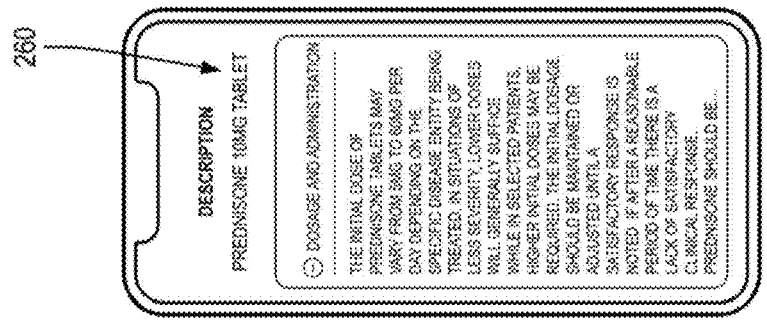
FIGS. 17A-17E are screen captures of a patient communication interface used with the system of FIG. 1.
Figure 17D:
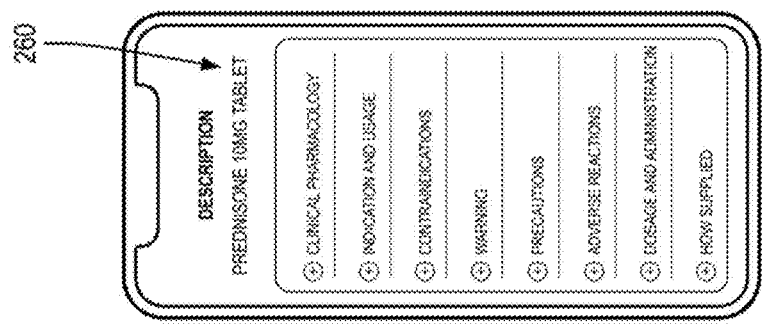
Figure 17C:
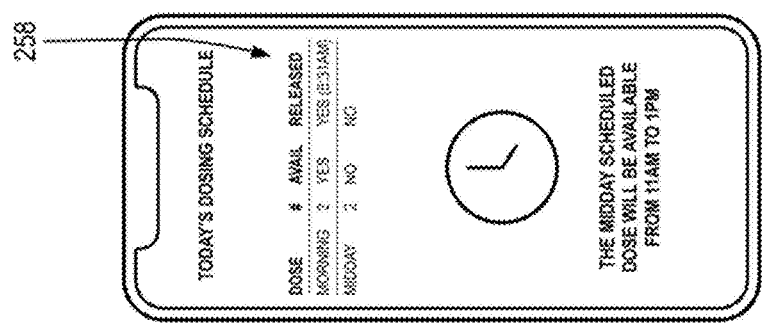
Figure 17B:
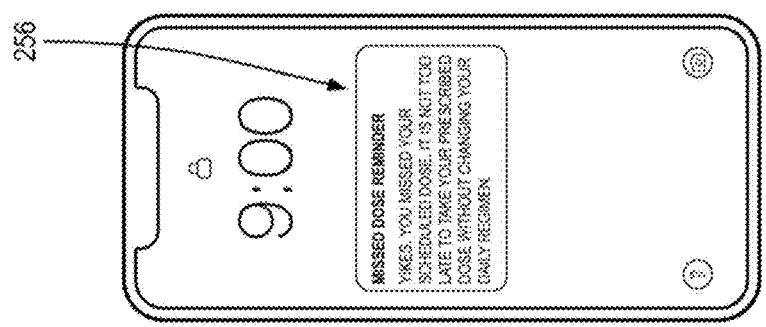
Figure 17A:
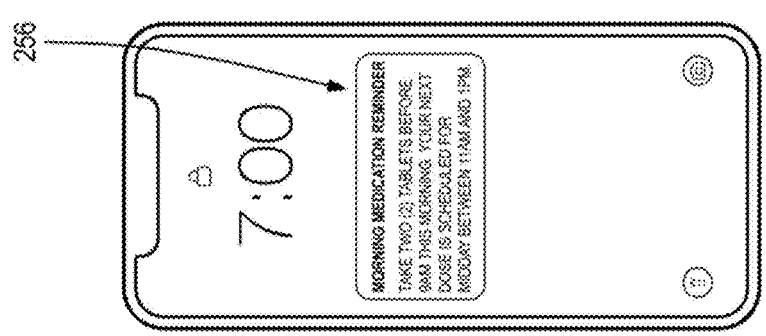

FIGS. 15 and 16 illustrate an example power management for the medication delivery station 102. For the shown implementation, the medication delivery station 102 is to be plugged into the wall with an inline DC power adaptor 210 prior to use. In the shown construction the adaptor 210 is coupled with a power main and the station at DC power connector 212. The medication delivery station 102 features an internal uninterruptible power supply (UPS) in case of a power loss event or power supply failure. The power management integrated circuit 180 provides regulated power for the operation of the medication delivery station 102. A backup battery 188 provides uninterruptible power to the device and is managed by a charge controller 182, protection circuitry 184, and a fuel gauge 186. The fuel gauge 186 provides both battery charge status and verification that an approved battery module is installed via interrogation of the authentication fuel gauge module 186 by the microcontroller 146. Of course, other implementations can be used for power management.

Remote monitoring of the actuation of the medication delivery station 102, dosing, and frequency of allowable use is monitored and controlled by an administration portal on a administration device 103 (FIG. 1). In addition to monitoring one or more of the above features, two-way communication between the medication delivery station 102 and the administration portal allow an administrator the ability to adjust any precision dosing parameters remotely and receive real-time feedback on its use. The administrator can be a health professional, a health agency or administrator, a governmental agency, and/or an insurer.

The wireless communication of the medication delivery station 102 permits the station 102 to pair with a remote communication host 101 (FIG. 1). As a result, some or all of the administration software or components may be housed separately from the medication delivery station 102. As indicated herein, releasing/delivering medication using the remote medication management system 100 is accomplished and controlled in conjunction with the use of administration software. Generally, the medication delivery station 102 is a stand-alone medication management system with enough onboard intelligence to receive and operate a dosing event command within the pre-set onboard parameters and executable instructions. In one or more particular examples, all of the parameters and settings for controlling the medication delivery process are stored onboard the medication delivery station 102 in the digital memory of its microcontroller 146. However, in alternative variations, less than all of the parameters and settings needed to control the medication delivery process are stored onboard the medication delivery station 102, in which case they be stored on the third-party host or other remote system.

It is also possible for the dosing regimen parameters to be altered remotely via a remote application. In this regard, in order for the dosing regimen parameters to be altered, the medication delivery station 102 should be "paired" to the remote communication host 101 and information sent to the host from an administrator device 103. Alternatively, one or more dosing regimen parameters may be altered on the medication delivery station 102. Dosing parameter manipulation and adjustment is controlled by administration software, and in the case of the remote system described above, uploaded to the medication delivery station 102 via the communication host 101 as commanded by the administration device 103. The dosing regimen parameters may remain resident on the medication delivery station 102 in the digital memory of the microprocessor until such time or times as a command to update data is received from the administrator device 103. Alternatively, parameters may be delivered in real-time. In the event of a loss of signal between the medication delivery station 102 and the communication host 101, the remote medication management system may act as a stand-alone unit delivering medication within the limits of the dosing regimen parameters last uploaded and stored on the medication delivery station 102.

In one or more implementations, the dosing regimen comprises a data packet. The data packet includes integers that populate preconfigured set point fields and form the basis of the dosing regimen criteria. A variety of dosing regimen criteria may be used and may be contemplated by one of skilled in the art in a manner suitable for the intended purposes. Alternative or additional criteria, such as a lapsed time period, and the like, may be used without departing from the overall scope of the system. The execution of each dosing event is controlled by the data packet. The microcontroller 146 monitors the total number of pills 112 that have been released with input from the weigh systems 144 and the camera and illumination system 132 and decrements the pill inventory from a value stored in memory on the medication delivery station 102 and medication closure container 110. The updated pill inventory value is communicated to the remote communication host 101 and can be communicated to the mobile applications on devices 103 and 105. As the contents of the medication closure container 110 are depleted and confirmed by the weigh systems 144 and the camera and illumination system 132, the pill inventory count is reduced and compared to one or more pre-established setpoint values. Immediately after each dosing event, the amount of dose inventory available or remaining in the closure container inventory is compared against pre-established trigger points and appropriate messages sent to the administrator application or mobile application. Once the closure container inventory indicates a value of zero, the medication delivery station 102 may await instructions from the remote communication host 101. The communication host 101 may instruct the medication delivery station 102 to prompt the user to remove the empty medication closure container 110 and to provide instructions on the recycling of the container 110. In some applications, the healthcare provider may end the prescription prior to depletion of the container 110. In some constructs, the closure container 110 can be inactivated by mechanical means via blockade of rotary motion of the inner plate 230. In some applications, the user may be instructed to return the container 110 to a pre-specified vendor for disposal of unused medications 112. If the communication host 101 indicates that a medication closure container refill 110B should be inserted into the station receptable 104, the mobile application prompts the user to insert the refill container 110B by pairing the alignment rails 236 with the rail guides 200 of the medication closure container 110B. Simultaneously, the administration portal sends a data packet to the station 102 with data on the refill medication closure container 110B and possibly updated dosing regimen parameters.

Data may be stored and transmitted by and within the system in any suitable form. Any source code or language suitable for accomplishing the desired functions described herein may be acceptable for use. The software system described herein may include a mixture of different source codes. The system or method herein may be operated by computer-executable instructions, such as but not limited to, program modules, executable on a computer. Examples of program modules include, but are not limited to, routines, programs, objects, components, data structures and the like which perform particular tasks or implement particular instructions. The software system may also be operable for supporting the transfer of information within a network.

Figure 18:
FIG. 18 is a screen capture of an administration portal for adaptive precision used with the system of FIG. 1.
Figure 19:
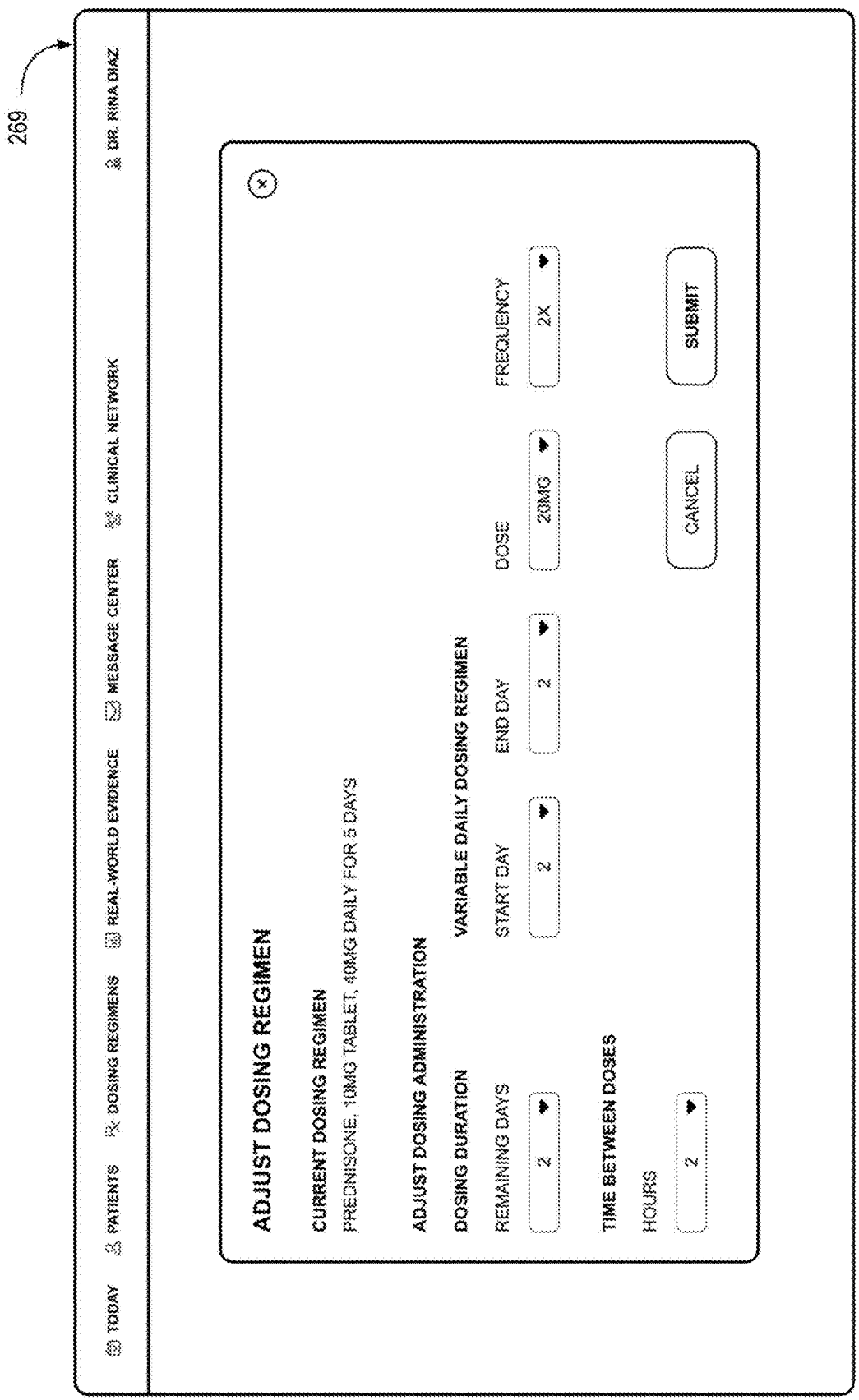
FIG. 19 is a screen capture of an administration portal for adaptive precision used with the system of FIG. 1.

The patient communication interface for the remote medication management system 100 in one implementation is a mobile application located on a user-controlled mobile electronic device 105. The mobile device 105 can be, without limitation, a smart phone, a smart tablet, a web device, a laptop computer, and many other similar devices. In the implementations discussed herein, the mobile device 105 is a smart phone. FIGS. 17A-17E provides examples of the embodiments of the patient communication interface, specifically the mobile application including medication notifications 256, current dosing schedule 258, and medication description 260. A screen 268 for the remote administration portal is displayed in FIG. 18. The screen 268 shows a unique serial number 262 of the closure container, initial dosing regimen 264, and the medication administration record 266. FIG. 19 provides the remote administration portal including a screen 269 by which the administrator adjusts the dosing regimen.

Figure 20:
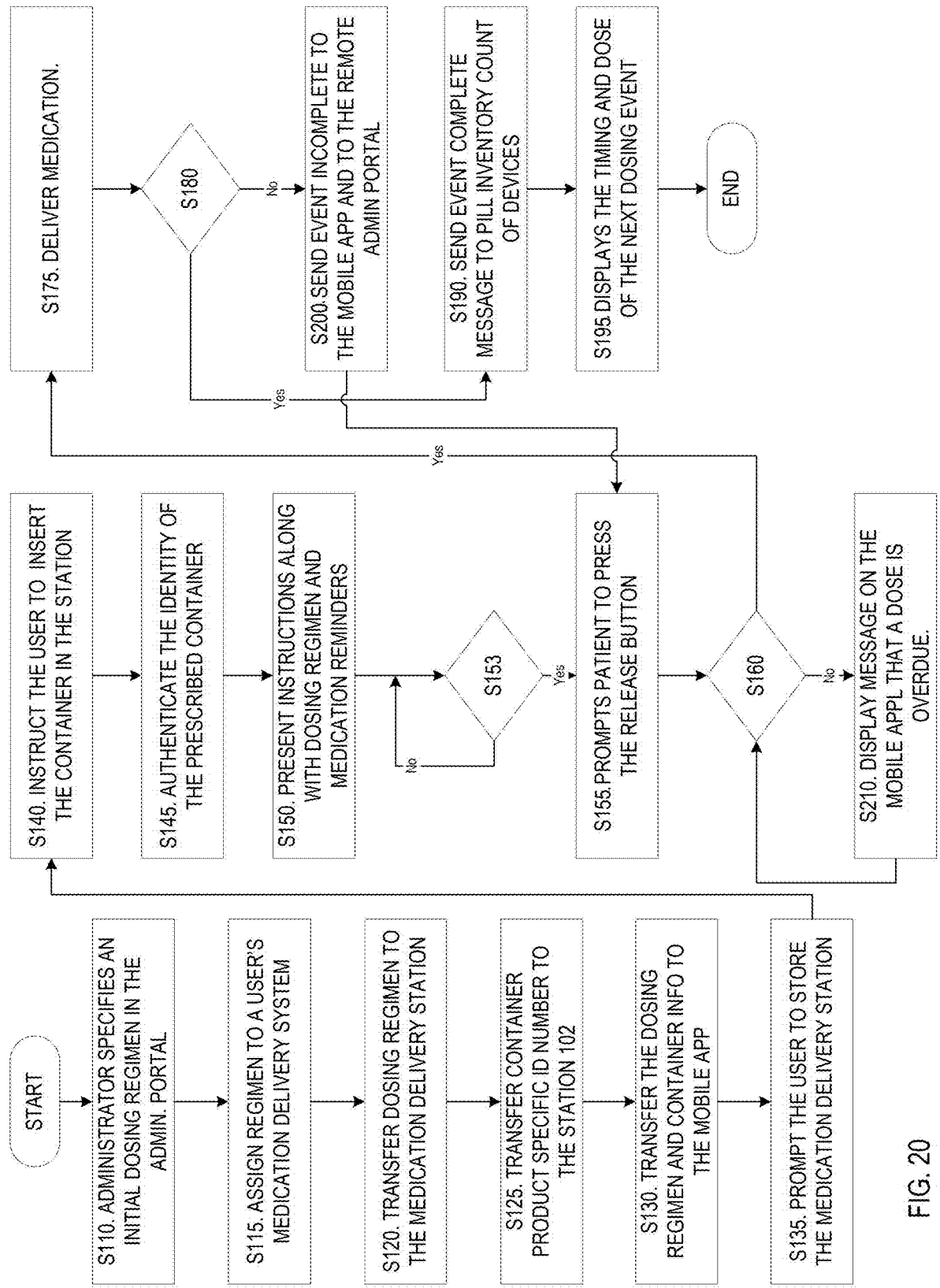
FIG. 20 is a flowchart representing the synchronization of the operation of the administration software and the medication delivery station.

The synchronization of the operation of the administration software and the medication delivery station 102 is described below and shown in FIG. 20. Upon prescribing a medication to be administered through the remote medication management system 100, an administrator (e.g., a clinician) specifies (step S110) an initial full dosing regimen in the administration portal 264. A specific medication delivery system with a unique identification code (e.g., an alphanumeric identifier) is assigned (step S115) to the user (e.g., patient) in the administration portal 262. The remote communication host (e.g., a third-party host server) communicates with the medication delivery station 102 and transfers (step S120) the initial full dosing regimen to the medication delivery station 102 for storage and use by the station administration software. The third-party host also transfers (step S125) the closure container product specific identification (e.g., serial number or alphanumeric code) to the medication delivery station 102. The station 102 communicates with the mobile application 258 through a BLE connection and transfers (step S130) the initial patient-specific dosing regimen and the closure container information to the mobile application 258. The mobile application 258 prompts (step S135) the user to store the medication delivery station 102 in a location in keeping with their needs. The mobile application 258 then instructs (step S140) the user to lift the lid 116 on the medication delivery station 102 and to insert the medication closure container 110 by pairing the alignment rails 236 on the medication closure container 110 with the alignment rail guides 200. Once paired, the medication delivery station 102 and the medical closure container 110 authenticate (step S145) the identity of the prescribed container 110. After container authentication, the mobile application (FIG. 17) presents (step S150) the startup and onboard instructions along with the current daily schedule dosing regimen and medication reminders 256. When a dosing event is authorized for immediate delivery (S153), the mobile application prompts (step S155) the patient to press the release button 170 on the front of the medication delivery station 102. When the release button 170 is depressed (S160), the delivery station administration software queries whether the current time is greater than a first preset medication release time for this dosing event. If this parameter has been met, then the station administrator confirms the approval of the dosing event at the specific time of request. The medication delivery station 102 is operated (step S175) to deliver x-number of pills 112 or a predetermined amount of medication. Once a successful dose delivery sequence has been completed (step S180) by the delivery station, it reports "dose event complete" or "dose event incomplete" (in the event of an error). The dose event complete message is sent (step S190) to the station and container closure pill inventory count, the mobile application, and the remote communication host 101. The mobile application displays (step S195) the timing and dose of the next dosing event 258. A dose incomplete (step S200) event is reported to the mobile application with specific instructions to the patient and to the remote administration portal. If the release button 170 has not been depressed during the time window that a dose event has been scheduled, a message is displayed (step S210) on the mobile application that a dose is overdue. In one or more examples, the software may deliver periodic push notifications to the user until it receives a message from the medication delivery station 102 that the dose has been delivered.

In some implementations, a dosing event may be incomplete if one or more pills 112 has been damaged during the delivery process. To detect if a dosing event delivered medication that has been broken, chipped, cracked, dented, or otherwise damaged, the camera subsystem 160 obtains multiple images of the pills 112 during the medication delivery release sequence. During delivery from the medication closure container 110 through the pill chute 206 and into the medication receptacle 120, one or more images of the pills 112 in motion are obtained and analyzed using spatial machine learning object detection models. Additional images are taken when the pills 112 reach the medication receptacle 120. The machine learning object detection models are trained and validated to classify damaged pills that should not be administered to the patient to meet the dosing requirement. If the machine learning object detection models confirm that some or all of the dose has been damaged, the medication delivery station 102 messages the mobile application and the administration portal 103 that a damaged incomplete dosing event has occurred. If the remote administrator has approved damaged pill replacement, the medication delivery station 102 repeats the dosing event to ensure the patient receives a full dose at this scheduled dosing event. If a second consecutive incomplete dosing event occurs, the medication delivery station 102 connects with the remote communication host 101 and notifies the remote administrator of the repeated failures.

The execution of each dosing event can be controlled by a data packet. The data packet may have information that populate preconfigured set point fields and form the basis of the dosing regimen parameters. The number of dosing events deployable within a given time frame may be controlled, as well as the total number of dosing events allowable between reloading of the data from the remote communication host 101. As indicated, in one or more examples if the medication delivery station 102 is not paired with the remote communication host 101, the total number of dosing events may be allowed or limited in keeping with the pre-loaded criteria.

Data may be sent or submitted via the Internet, wireless, cellular, and fiber-optic communication networks or created or stored on a particular device such as an edge, internet of things device. In one or more examples, data, such as but not limited to, instructions, identifiers, parameters, sensors, analytic or usage data may be stored on the medication delivery station 102 in the storage 150. In one or more examples, data may be stored remotely or may be stored locally on a patient electronic device and/or in the mobile application 124. However, data may also be stored remotely or retrieved. Locally created content or data may also be used and stored. Data may be stored and transmitted by and within the system in any suitable form. Any source code or other language suitable for accomplishing the desired functions described herein may be acceptable for use.

In some implementations, a communication interface (e.g. LCD screen 106) on the medication delivery station 102C may be provided or accessible through the delivery station housing. The patient interacts with the communication interface on the medication delivery station 102 rather than a mobile application. To alert the patient of the need for medication, a speaker system with buzzers and voice commands can prompt the user for the time to administer a dose. In some constructions, a visual status indicator using a single colored or flashing light (e.g. red-green-blue (RGB) light emitting diode (LED)) or a plurality of colored or flashing lights provides additional visual feedback to the patient during interaction with the device.

The remote medication management system 100 described in one or more examples is for use with oral solid medication of all sizes and shapes including round pills, hard and soft-shelled capsules, and a variety of oval pills. In one or more examples, the medication delivery station 102B can be configured with one or more receptacles 104 to release multiple medications from the same station 102B. In the multiple receptacle delivery station 102B, different dose strengths of the same medication can be stored and delivered to the patient in a single dosing event. For example, a patient may be prescribed 17.5 mg of a drug and the available dose strengths are 0.5 mg, 1 mg, and 5 mg. The delivery station administration software determines the specific number of pills 112 from each dose strength based on the current pill inventory. For the 17.5 mg dosing requirement, three 5 mg pills, two 1 mg pills, and one 0.5 mg pills could be released into the medication cup to meet the total dosing strength requirement. In another example, the dosing requirement could be satisfied with three 5 mg pills, and five 0.5 mg pills. One or more medications could also be delivered during the same dosing event or at different dosing times to ensure optimal therapeutic response to a set of medications. In another variation, three separate single medication delivery stations 102 can be used to manage three medications with a central hub either on one station or coordinated with a remote administration portal.

Furthermore, a computer or computers or portable electronic devices, such as an edge internet of things device, may be operatively or functionally connected to one or more medication delivery stations 102. In one or more examples, the computer or portable electronic device may act or operate as a "server" storing one or more data files (e.g. dosing regimen parameters) for use by the administration software and the communication interface. The computer or portable electronic device may also utilize an Internet-connected website, provided to manage one or more functions of the software system and communication interface operated by the portable electronic device. In other words, the portable electronic device, software applications, communication interface, personal computer, and website may be integrated for use.

In one or more examples, the remote medication management system 100 can be used in a healthcare facility such as a clinic, skilled nursing, rehabilitation hospital or an acute-care hospital. In these settings, the remote medication management system 100 can be used by the patients independently in their treatment or hospital rooms without needing complete nursing oversight for the administration of the medication.

In one or more examples, the material of the remote medication management system 100 may be formed of a durable material. In one or more further examples, the material may be formed of a sterile material, or a material suitable for the containment and storage of and/or stability of medication. In one or more particular examples, components herein may be composed of a plastic or polymeric materials or resins. Combinations of materials may also be acceptable, such as but not limited to, a motor with one or more aluminum, stainless-steel or other metal gears or interfaces and a polymeric housing. Various sealants and joint seals known in the art may be used without departing from the overall scope of the present invention.

In various implements, one or more medication delivery station 102 and/or closure container components are formed by molding and subsequently assembled by methods including but not limited to joining by adhesives, ultrasonic welding, fasteners, or other joining methods to form subassemblies or components described herein. Likewise, in one or more examples, the remote medication management system 100 may be provided with an appropriate environmental seal which maintains the integrity and/or stability of the medication contained therein.

In another implementation, the LCD screen 106 of the station 102C replaces the mobile application as the screen for notifications, alerts, and information on the dosing schedule and pill inventory available in the container.

While this invention has been described in conjunction with the examples of the embodiments above, various alternatives, modifications, variations, improvements and/or substantial equivalents, whether known or that are or may be presently foreseen, may become apparent to those having at least ordinary skill in the art. Accordingly, the examples of embodiments of the invention, as set forth above, are intended to be illustrative, not limiting. Various changes may be made without departing from the spirit or scope of the invention. Therefore, the invention is intended to embrace known or earlier developed alternatives, modifications, variations, improvements, and/or substantial equivalents.

Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts and vice versa, the operation of the interfaces may be reversed or otherwise varied, the length or width of the structures and/or members or connectors or other elements of the system may be varied, the nature or number of adjustment positions provided between the elements may be varied (e.g., by variations in the number of engagement slots or size of the engagement slots or type of engagement). The order or sequence of any process or method steps may be varied or re-sequenced according to alternative embodiments. Other substitutions, modifications, changes, and omissions may be made in the design, operating conditions, and arrangement of the various examples of embodiments without departing from the spirit or scope of the present inventions.

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B, C" includes A only, B only, C only, or any combination thereof (e.g., AB, AC, BC, or ABC).

For the purpose of this disclosure, the term "coupled" means the joining of two members directly or indirectly to one another. Such joining may be stationary in nature or moveable in nature. Such joining may be achieved with the two members, or the two members and any additional intermediate members being integrally formed as a single unitary body or with the two members or the two members and any additional intermediate members being attached to one another. Such joining may be permanent in nature or may be removable or releasable in nature.

The terms fixedly, non-fixedly, and removably, and variations thereof, may be used herein. The term fix, and variations thereof, refer to making firm, stable, or stationary. It should be understood, though, that fixed does not necessarily mean permanent—rather, only that a significant or abnormal amount of works needs to be used to make unfixed. The term removably, and variations thereof, refer to readily changing the location, position, and/or station. Removably is meant to be the anonym of the term fixedly. Alternatively, the term non-fixedly can be used as the antonym of fixedly.

Preferences and options for a given aspect, feature or parameter of the disclosure should, unless the context indicates otherwise, be regarded as having been disclosed in combination with any and all preferences and options for all other aspects, features, and parameters of the disclosure.

Aspects and constructions herein can be embodied in other forms without departing from the spirit or essential attributes thereof. Accordingly, reference should be made to the following claims, rather than to the foregoing specification, as indicating the scope hereof

What is claimed is:

1. A medication management system comprising:
a replaceable substantially cylindrical pre-filled oral solid medication storage and closure container comprising:
  a plurality of pills;
  a substantially cylindrical sealed housing having an alignment rail along a length of the sealed housing, and a first aperture in the sealed housing allowing for discharge of the plurality of pills;
  a closure opening and sealing the sealed housing at the first aperture;
  a first communication interface coupled to the sealed housing;
  a read-write memory coupled to the first communication interface, the read-write memory having information including a container-specific identifier, a medication-specific identifier, and a medication inventory status; and
a medication delivery station comprising:
  a housing having a substantially cylindrical receptacle with a rail guide, the medication closure container being removably disposed in the receptacle with the alignment rail disposed in the rail guide, and a chute to receive the plurality of pills from the medication closure container;
  a second communication interface coupled to the housing and in wired communication with the first communication interface; and
  a processor and a memory in communication with the processor, the processor and memory coupled within the housing, the memory including instructions executable by the processor to
    communicate with the medication closure container via the second communication interface and the first communication interface,
    receive the container-specific identifier, the medication-specific identifier, and the medication inventory status, and
    confirm the container-specific identifier.

2. The system of claim 1, wherein the first communication interface includes a first hardware communication interface coupled to the sealed housing, wherein the second communication interface includes a second hardware communication interface supported by the housing within the receptacle, and wherein the first hardware communication interface directly connects to the second hardware communication interface when the medication closure container is disposed in the receptacle.

3. The system of claim 1, wherein the medication inventory status includes a prefilled medication amount and a current medication inventory status.

4. The system of claim 1, wherein the information further includes expected user information for the medication closure container and an expected medication delivery station for the medication closure container, wherein the memory further includes station information including user information and a delivery station identification, and wherein the memory further includes instructions executable by the processor to compare the expected user information and the expected medication delivery station with the user information and the deliver station identification, respectively.

5. The system of claim 1, wherein the medication delivery station further comprises an optical sensor supported by the housing and optically sensing towards the receptacle, wherein the sealed housing includes a translucent window disposed in the sealed housing and the optical sensor senses movement within the medication closure container via the translucent window.

6. The system of claim 1, wherein the medication closure container further comprises a drive system interface, and wherein the station further comprises a drive coupled with the drive system interface, the drive including a stepper motor and a stepper motor controller coupled to the processor.

7. The station of claim 1, further comprising a removeable receptacle disposed within a dispensing compartment.

8. The station of claim 7, further comprising a weigh system coupled to the processor and adjacent with the dispensing compartment, and wherein the memory including further instructions executable by the processor to weigh content of the removeable receptacle.

9. The station of claim 7, further comprising a camera system coupled to the processor and adjacent with the dispensing compartment, and wherein the memory including further instructions executable by the processor to capture an image of content of the removeable receptacle.

10. The system of claim 1, further comprising:
a user-controlled electronic device in communication with the station;
an administrator portal in communication with the station via a wireless communication interface; and
a host server in communication with the station via the wireless communication interface.

11. The medication management system of claim 1, wherein the medication closure container further comprises a translucent window coupled to the sealed housing of the medication closure container, wherein the medication delivery station further comprises an optical sensor supported by the housing of the medication delivery station, and wherein the memory includes instructions further executable by the processor to sense movement within the medication closure container through the translucent window via the optical sensor.

12. The medication management system of claim 11, wherein the substantially cylindrical sealed housing has a first end surface, a second end surface, and a side surface between the first end surface and the second end surface, wherein the side surface includes the alignment rail, and the first end surface includes the first communication interface and the translucent window.

13. An automated and adaptable remote management system, the system comprising:
the medication management system of claim 1;
a user-controlled electronic device in communication with the medication delivery station; and
a remote administration portal in communication with the medication delivery station.

14. The automated and adaptable remote management system of claim 13, further comprising a remote host server in communication with the remote administration portal and in further communication with the medical delivery station.

15. A method for remotely managing and adapting precision dosing of the automated and adaptable remote management system of claim 13, the method comprising:
coupling the medication closure container with the medication delivery station;
communicating medication closure container product specific identification to the medication delivery station; and
authenticating the medication closure container with the medication delivery station.

16. The method of claim 15, wherein the medication closure container product specific identification includes an expected container-specific identifier for the medication delivery station.

17. The method of claim 15, wherein the medication closure container product specific identification includes an expected medication-specific identifier and an expected medication inventory status.

18. The method of claim 15, wherein communicating medication closure container product specific identification includes communicating to the medication delivery station an expected container-specific identifier, an expected medication-specific identifier, and an expected medication inventory status, and wherein authenticating the medication closure container with the medication delivery station includes comparing an expected container-specific identifier, an expected medication-specific identifier, and an expected medication inventory status with the container-specific identifier, the medication-specific identifier, and the medication inventory status.

19. The method of claim 15, the method further comprising:
receiving an initial patient-specific dosing regimen at the remote administrator portal; and
communicating the initial patient-specific dosing regimen to the medication delivery station.

20. The method of claim 19, the method further comprising, after communicating the initial patient-specific dosing regimen to the medication delivery station, communicating the initial patient-specific dosing regimen to the medication delivery station to the user-controlled electronic device.

21. The method of claim 19, the method further comprising:
receiving, at the user-controlled electronic device, input from a user on a pendency of symptoms;
communicating the symptoms to the remote administration portal;
receiving a revised patient-specific dosing regimen at the remote administrator portal; and
communicating the revised patient-specific dosing regimen to the medication delivery station.

22. The method of claim 15, the method further comprising:
- receiving a signal requesting dispensing of a dose of medication; and
- querying whether the dose of medication can be dispensed.

23. The method of claim 22, the method further comprising dispensing one or more pills if the dose of medication can be dispensed, the one or more pills corresponding to the dose of medication.

24. The method of claim 23, the method further comprising:
- after dispensing the one or more pills, communicating the dispensing of the medication to the medication closure container, the medication delivery station, and the remote administration portal; and
- updating medication inventor status at each of the medication closure container, the medication delivery station, and the remote administration portal.

* * * * *